(12) United States Patent
Monia et al.

(10) Patent No.: US 6,784,290 B1
(45) Date of Patent: Aug. 31, 2004

(54) ANTISENSE OLIGONUCLEOTIDE INHIBITION OF RAS

(75) Inventors: Brett P. Monia, LaCosta, CA (US); Lex M. Cowsert, Carlsbad, CA (US); Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 1162 days.

(21) Appl. No.: 09/575,554

(22) Filed: May 22, 2000

Related U.S. Application Data

(63) Continuation-in-part of application No. 09/128,494, filed on Aug. 3, 1998, now Pat. No. 6,117,848, which is a continuation of application No. 08/889,296, filed on Jul. 8, 1997, now Pat. No. 5,872,242, which is a continuation-in-part of application No. 08/411,734, filed as application No. PCT/US93/09346 on Oct. 1, 1993, which is a continuation-in-part of application No. 08/007,996, filed on Jan. 21, 1993, now abandoned, and a continuation-in-part of application No. 07/958,134, filed on Oct. 5, 1992, now abandoned.

(51) Int. Cl.[7] .................. C07H 21/02; C07H 21/04; A61K 30/70

(52) U.S. Cl. .................. 536/24.5; 514/44; 435/6; 435/91.2; 536/23.1; 536/24.3

(58) Field of Search ................ 536/24.5, 231, 536/243; 514/44; 435/6, 91.2

(56) References Cited

U.S. PATENT DOCUMENTS

| | | | |
|---|---|---|---|
| 4,871,838 A | 10/1989 | Bos et al. | 536/27 |
| 5,034,506 A | 7/1991 | Summerton et al. | 528/391 |
| 5,138,045 A | 8/1992 | Cook et al. | 536/27 |
| 5,218,105 A | 6/1993 | Cook et al. | 536/25.31 |
| 5,378,825 A | 1/1995 | Cook et al. | 536/25.34 |
| 5,459,255 A | 10/1995 | Cook et al. | 536/27.13 |
| 5,576,208 A | * 11/1996 | Monia et al. | 435/375 |
| 5,582,986 A | * 12/1996 | Monia et al. | 435/6 |
| 5,591,582 A | * 1/1997 | Bos et al. | 435/6 |
| 5,872,242 A | * 2/1999 | Monia et al. | 536/24.5 |

FOREIGN PATENT DOCUMENTS

| | | |
|---|---|---|
| WO | PCT/US88/01024 | 3/1988 |
| WO | WO 92/15680 | 9/1992 |
| WO | WO 94/26764 | 11/1994 |

OTHER PUBLICATIONS

Ott et al (Biochemistry (1987) 26:8237–8241).*

Manoharan et al (Tetrahedron Letters (1991) 32:7171–7174).*

Anfossi et al., "An Oligomer Complementary to c–myb–encoded mRNA inhibits proliferation of human myeloid leukemia cell lines", Proc. Natl. Acad. Sci. 1989, 86, 3379–3383.

Borer, P.N., Dengler, B., Tinoco, I., Jr., and Uhlenbeck, O.C., "Stability of Ribonucleic acid Double–stranded Helices", J. Mol. Biol., 1974, 86, 843–853.

Brown et al., "Modulation of ras Expression by Anti–sense, Nonionic Deoxyoligonucleotide Angalogs", Oncogene Research 1989, 4, 243–252.

Capon et al., "Complete nucleotide sequence of the T24 human bladder carcinoma oncogene and its normal homologue", Nature 302 1983, 33–37.

Chang et al., "Comparative inhibition of ras p21 protein synthesis with phosphorus–modified antisense oligonucleotides", Anti–Cancer Drug Design 1989, 4, 221–232.

Chang et al., "Antisense inhibition of ras p21 expression that is sensitive to a point mutation", Biochemistry 1991, 30, 8283–8286.

Chiang et al., "Antisense Oligonucleotides Inhibit Intercellular Adhesion Molecule 1 Expression by Two Distinct Mechanisms", J. Biol. Chem. 1991, 266:18162–18171.

De Mesmaeker et al., "Anitsense Oligonucleotides", Acc. Chem. Res. 1995, 28:366–374.

Dignam et al., "Accurate transcription initiation by RNA polymerase II in a soluble extract from Isloated mammalian nuclei", Nucleic Acids Res. 1983, 11, 1475–1489.

Feramisco et al., "Transient reversion of ras oncogene–induced cell transformation by antibodies specific for amino acid 12 of ras protein", Nature 1985, 314, 639–642.

Gebeyehu, G., et al., "Novel biotinylated nucleotide—analogs for labeling and colorimetric detection of DNA", Nucl. Acids Res. 1987, 15:4513–4534.

Georges, R.N. et al., "Prevention of Orthotopic Human Lung Cancer Growth by Intratracheal Instillation of a Retroviral Antisense K–ras Construct", 1993, Cancer Research, 53, 1743–1746.

Greenberg, M.E., in Current Protocols in Molecular Biology, (F.M. Ausubel, R. Brent, R.E. Kingston, D.D. Moore, J.A. Smith, J.G. Seidman and K. Strahl, eds.), John Wiley and Sons, NY.

Hall et al., "Identificaiton of transforming gene in two human sarcoma cell lines as a new member of the ras gene family located on chromosome 1", Nature 1983, 303: 396–400.

(List continued on next page.)

Primary Examiner—Jeffrey Fredman
(74) Attorney, Agent, or Firm—Licata & Tyrrell P.C.

(57) ABSTRACT

Compositions and methods are provided for the modulation of ras expression. Oligonucleotides are provided which are targeted to nucleic acids encoding human ras. Oligonucleotides specifically hybridizable with mRNA encoding human H-ras, Ki-ras and N-ras are provided. Such oligonucleotides can be used for therapeutics and diagnostics as well as for research purposes. Methods are also disclosed for modulating ras gene expression in cells and tissues using the oligonucleotides provided, and for specific modulation of expression of activated ras. Methods for diagnosis, detection and treatment of conditions, or particular cancers, associated with ras are also disclosed.

15 Claims, 12 Drawing Sheets

OTHER PUBLICATIONS

Hall and Brown, "Human N–ras: cDNA cloning and gene structure", *Nucleic Acids Res.* 1985, 13, 5255–5268.

Holt et al., "An Oligomer Complementary to c–myc mRNA Inhibits Proliferation of HL–60 Promyelocytic Cells and Induces Differentiation", *Mol. Cell Biol.* 1988, 8, 963–973.

Kabanov et al., "A new class of antivirals: antisense oligonucleotides combined with a hydrophobic substituent effectively inhibit influenza virus reproduction and synthesis of virus–specific proteins in MDCK cells", *FEBS Lett.* 1990, 259, 327–330.

Kahn et al., The c–K–ras gene and human cancer (review), *Anticancer Res.* 1987, 7, 639–652.

Kawasaki et al., "Uniformly Modified 2'–Deoxy-2'–fluoro Phosphorothioate Oligonucleotides as Nuclease–Resistant Antisense Compounds with High Affinity and Specificity for RNA Targets", *J. Med. Chem.* 1993, 36, 831–841.

Kingston, R.E., in *Current Protocols in Molecular Biology*, (F.M. Ausubel, R. Brent, R.E. Kingston, D.D. Moore, J.A. Smith, J.G. Seidman and K. Strahl, eds.), John Wiley and Sons, NY.

Kornberg, A., *DNA Replicaiton*, W.H. Freeman & Co., San Francisco, 1980, pp 75–77.

Lima et al., "Implication of RNA Structure of Antisense Oligonucleotide Hybridization Kinetics", *Biocehmistry* 1992, 31, 12055–12061.

Letsinger et al., "Cholesteryl–conjugated oligonculeotides: Synthesis, properties, and activity as inhibitors of replication of human immunodeficiency virus in cell culture", *Proc. Natl. Acad. Sci.* USA 1989, 86, 6553–6556.

Mukhopadhyay, T. et al., "Specific Inhibition of K–ras Expression and Tumorigenicity of Lung Cancer Cells by Antisense RNA", (1991) *Cancer Research* 51, 1744–1748.

Martin, P., "Ein neuer Zugang zu 2'–O–Alkylribonucleosiden und Eigenschaften deren Oligonucleotide", *Helv. Chim. Acta* 1995, 78, 486–504.

Manoharan et al., "Cholic Acid–Oligonucleotide Conjugates for Antisense Applications", *Bioorg. Med. Chem. Let.* 1994, 4, 1053–1060.

Manoharan et al., "Introduction of a Lipophilic Thioether Tether in the Minor Groove of Nucleic Acids for Antisense Applications", *Bioorg. Med. Chem. Let.* 1993, 3, 2765–2770.

Manoharan et al., "Anitsense Strategies", *Ann. N.Y. Acad. Sci.* 1992, 660, 306–309.

Manoharan et al., "Lipidic Nucleic Acids", *Tetrahedron Lett.* 1995, 36, 3651–3654.

Manoharan et al., "Oligonucleotides Conjugates: Alteration of the Pharmacokinetic Properties of Anitsense Agents", *Nucleosides& Nucleotides* 1995, 14, 969–973.

McGrath, J.P. et al., "Structure and organization of the human Ki–ras proto–oncogene and a related processed pseudogene", *Nature* 1983, 304, 501–506.

Nielsen et al., "Sequence–Selective Recognition of DNA by Strand Displacement with a Thymine–Substituted Polyamide", *Science* 1991, 254, 1497.

Oberhauser et al., "Effective incorporation of 2'–o–methyl–oligoribonucleotides into liposomes and enhanced cell association through modification with thiocholesterol", *Nucl. Acids Res.* 1992, 20, 533–538.

Owen et al., "Transcriptional activation of a conserved sequence element by *ras* requires a nuclear factor distinct from c–fos or c–jun", *Proc. Natl. Acad. Sci. U.S.A.* 1990, 87, 3866–3870.

Petersheim, M. and Turner, D.H., "Base Stacking and Base–Pairing Contributions to Helix Stability: Thermodynamics of Double–Helix Formation with CCGG, CCGGp, CCG-GAp, ACCGGp, CCGGUp, and ACCGGUp", *Biochemistry* 1983, 22, 256–263.

Puglisi and Tinoco, "Absorbance Melting Curves of RNAs", *Methods in Enzymol.* 1989, 180, 304–325.

Reddy, P.E. et al., "A point mutation is responsible for the acquisition of transforming properties by the T24 human bladder carcinoma oncogene", *Nature* 1982, 300, 149–152.

Sanghvi et al., "Antisense oligodeoxynucleotides: synthesis; biophysical and biological evaluation of oligodeoxynucleotides containing modified pyrimidines", *Nucl. Acids Res.* 1993, 21, 3197–3203.

Sanghvi, Y.S., in Crooke, S.T. and Lebleu, B., eds., *Antisense Research and Applications*, CRC Press, Boca Raton, 1993, pp. 276–288.

Saison–Behmoaras, T. et al., "Short modified antisense oligonucleotides directed against Ha–*ras* point mutation selective cleavage of the mRNA and inhibit T24 cells proliferation", *EMBO J.* 1991, 10, 1111–1118.

Skorski, et al., "Growth Factor–dependent Inhibition of Normal Hematopiesis by N–*ras* Antisense Oligodeoxynucleotides", *J. Exp. Med.*, 1992, 175, 743–750.

Svinarchuk et al., "Inhibition of HIV proliferation in MT–4 cells by antisense oligonucleotide conjugated to lipophilic groups", *Biochimie* 1993, 75, 49–54.

Shea, "Synthesis, hybridization properties and antiviral activity of lipid–oligodeoxynucleotide conjugates", et al. *Nucl. Acids Res.* 1990, 18, 3777–3783.

Tidd et al., "Evaluation of N–*ras* oncogene anti–sense, sense and nonsense sequence methylphosphonate oligonucleotide analogues", *Anti–Cancer Drug Design* 1988, 3, 117–127.

Tabin, C.J. et al., "Mechanism of activation of a human oncogene", *Nature* 1982, 300, 143–149.

Taparowsky, E. et al., "Activation of the T24 bladder carcinoma transforming gene is linked to a signle amino acid change", *Nature* 1982, 300, 762–765.

Taparowsky et al., "Structure and Activation of the Human N–*ras* Gene", *Cell* 1983 34: 581–6.

Wickstrom et al., "Human promyelocytic leukemia HL–60 cell proliferation and *c–myc* protein expression are inhibited by an antisense pentadecadeoxynucleotide targeted against *c–myc* mRNA", *Proc. Nat. Acad. Sci.* 1988, 85, 1028–1032.

\* cited by examiner

```
                       SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 1:

CTTATATTCC GTCATCGCTC                                               20

(2) INFORMATION FOR SEQ ID NO: 2:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 2:

TCCGTCATCG CTCCTCAGGG                                               20

(2) INFORMATION FOR SEQ ID NO: 3:

(i) SEQUENCE CHARACTERISTICS:
         (A) LENGTH: 17
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 3:

CCACACCGAC GGCGCCC                                                  17

(2) INFORMATION FOR SEQ ID NO: 4:
```

```
        (i) SEQUENCE CHARACTERISTICS:
            (A) LENGTH: 19
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 4:

CCCACACCGA CGGCGCCCA                                                19

(2) INFORMATION FOR SEQ ID NO: 5:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 5:

GCCCACACCG ACGGCGCCCA C                                             21

(2) INFORMATION FOR SEQ ID NO: 6:

(i) SEQUENCE CHARACTERISTICS:
            (A) LENGTH: 23
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 6:

TGCCCACACC GACGGCGCCC ACC                                           23

(2) INFORMATION FOR SEQ ID NO: 7:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 7:

TATTCCGTCA TCGCTCCTCA                                               20

(2) INFORMATION FOR SEQ ID NO: 8:

(i) SEQUENCE CHARACTERISTICS:
            (A) LENGTH: 5
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 8:

CGACG                                                               5

(2) INFORMATION FOR SEQ ID NO: 9:

(i) SEQUENCE CHARACTERISTICS:
            (A) LENGTH: 7
            (B) TYPE: Nucleic Acid
```

```
            (C) STRANDEDNESS: Single
            (D) TOPOLOGY: Linear (iv) ANTI-SENSE: Yes (xi) SEQUENCE DESCRIPTION: SEQ ID NO: 9:

CCGACGG                                                                  7

(2) INFORMATION FOR SEQ ID NO: 10:

(i) SEQUENCE CHARACTERISTICS:
            (A) LENGTH: 9
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 10:

ACCGACGGC                                                                9

(2) INFORMATION FOR SEQ ID NO: 11:

(i) SEQUENCE CHARACTERISTICS:
            (A) LENGTH: 11
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 11:

CACCGACGGC G                                                            11

(2) INFORMATION FOR SEQ ID NO: 12:

(i) SEQUENCE CHARACTERISTICS:
            (A) LENGTH: 13
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 12:

ACACCGACGG CGC                                                          13

(2) INFORMATION FOR SEQ ID NO: 13:

(i) SEQUENCE CHARACTERISTICS:
            (A) LENGTH: 15
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 13:

CACACCGACG GCGCC                                                        15

(2) INFORMATION FOR SEQ ID NO: 14:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes
```

(xi) SEQUENCE DESCRIPTION: SEQ ID NO: 14:

CCACACCGAC GGCGCC                                                              16

(2) INFORMATION FOR SEQ ID NO: 15:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

CACACCGACG GCGCCC                                                              16

(2) INFORMATION FOR SEQ ID NO: 16:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 16:

CCCACACCGA CGGCGCCC                                                            18

(2) INFORMATION FOR SEQ ID NO: 17:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 17:

CCACACCGAC GGCGCCCA                                                            18

(2) INFORMATION FOR SEQ ID NO: 18:

(i) SEQUENCE CHARACTERISTICS:
        (A) LENGTH: 25
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 18:

TTGCCCACAC CGACGGCGCC CACCA                                                    25

(2) INFORMATION FOR SEQ ID NO: 19:

(i) SEQUENCE CHARACTERISTICS:
        (A) LENGTH: 17
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

CCACACCGCC GGCGCCC                                                             17

(2) INFORMATION FOR SEQ ID NO: 20:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20

CTGCCTCCGC CGCCGCGGCC                                      20

(2) INFORMATION FOR SEQ ID NO: 21:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

CAGTGCCTGC GCCGCGCTCG                                      20

(2) INFORMATION FOR SEQ ID NO: 22:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

AGGCCTCTCT CCCGCACCTG                                      20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

TTCAGTCATT TTCAGCAGGC                                      20

(2) INFORMATION FOR SEQ ID NO: 24:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

TTATATTCAG TCATTTTCAG                                      20

(2) INFORMATION FOR SEQ ID NO: 25:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 25:

CAAGTTTATA TTCAGTCATT                                                          20

(2) INFORMATION FOR SEQ ID NO: 26:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 26:

GCCTACGCCA CCAGCTCCAA C                                                        21

(2) INFORMATION FOR SEQ ID NO: 27:

(i) SEQUENCE CHARACTERISTICS:
            (A) LENGTH: 17
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 27:

CTACGCCACC AGCTCCA                                                             17

(2) INFORMATION FOR SEQ ID NO: 28:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 28:

GTACTCCTCT TGACCTGCTG T                                                        21

(2) INFORMATION FOR SEQ ID NO: 29:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 29:

CCTGTAGGAA TCCTCTATTG T                                                        21

(2) INFORMATION FOR SEQ ID NO: 30:

(i) SEQUENCE CHARACTERISTICS:
            (A) LENGTH: 20
            (B) TYPE: Nucleic Acid
            (C) STRANDEDNESS: Single (D) TOPOLOGY: Linear (iv) ANTI-SENSE: Yes (xi) SEQUENCE DESCRIPTION: SEQ ID NO: 30:

GGTAATGCTA AAACAAATGC                                               20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

GGAATACTGG CACTTCGAGG                                               20

(2) INFORMATION FOR SEQ ID NO: 32:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 32:

TACGCCAACA GCTCC                                                    15

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

TTTTCAGCAG GCCTCTCTCC                                               20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

TCAGTAATAG CCCCACATGG                                               20

(2) INFORMATION FOR SEQ ID NO: 35:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

CCGGGTCCTA GAAGCTGCAG                                           20

(2) INFORMATION FOR SEQ ID NO: 36:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

TAAATCAGTA AAAGAAACCG                                           20

(2) INFORMATION FOR SEQ ID NO: 37:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 37:

GGACACAGTA ACCAGGCGGC                                           20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

AACAGAAGCT ACACCAAGGG                                           20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

CAGACCCATC CATTCCCGTG                                           20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

GCCAAGAAAT CAGACCCATC                                           20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

AGGGGGAAGA TAAAACCGCC                                              20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 42:

CGCTTCCATT CTTTCGCCAT                                              20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 43:

CCGCACCCAG ACCCGCCCCT                                              20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

CAGCCCCCAC CAAGGAGCGG                                              20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

GTCATTTCAC ACCAGCAAGA                                              20

(2) INFORMATION FOR SEQ ID NO: 46:

(i) SEQUENCE CHARACTERISTICS:

(A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

CAGTCATTTC ACACCAGCAA                                               20

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

CTCAGTCATT TCACCAGC                                                 20

(2) INFORMATION FOR SEQ ID NO: 48:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

CGTGGGCTTG TTTTGTATCA                                               20

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CCATACAACC CTGAGTCCCA                                               20

(2) INFORMATION FOR SEQ ID NO: 50:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

CAGACAGCCA AGTGAGGAGG                                               20

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear

```
    (iv) ANTI-SENSE: Yes (xi) SEQUENCE DESCRIPTION: SEQ ID NO: 51:

CCAGGGCAGA AAAATAACAG                                           20

(2) INFORMATION FOR SEQ ID NO: 52:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

TTTGTGCTGT GGAAGAACCC                                           20

(2) INFORMATION FOR SEQ ID NO: 53:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 53:

GCTATTAAAT AACAATGCAC                                           20

(2) INFORMATION FOR SEQ ID NO: 54:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 54:

ACTGATCACA GCTATTAAAT                                           20

(2) INFORMATION FOR SEQ ID NO: 55:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 55:

GCCGAGGTCC ATGTCGTACG C                                         21
```

ANTISENSE OLIGONUCLEOTIDE INHIBITION OF RAS

INTRODUCTION

This application is a continuation-in-part of application Ser. No. 09/128,494, filed Aug. 3, 1998, now U.S. Pat. No. 6,117, 848, which is a continuation of application Ser. No. 08/889,296, filed Jul. 8, 1997, and issued Feb. 16, 1999 as U.S. Pat. No. 5,872,242, which is a continuation-in-part of U.S. patent application Ser. No. 08/411,734, filed Apr. 3, 1995 which is a U.S. national phase application-of PCT/US93/09346, filed Oct. 1, 1993, which is a continuation-in-part and foreign filing of U.S. patent application Ser. No. 08/007,996, filed Jan. 21, 1993 now abandoned and U.S. patent application Ser. No. 07/958,134, filed Oct. 5, 1992, now abandoned and all of which are assigned to the assignee of the present invention and are incorporated herein by reference in their entirety.

FIELD OF THE INVENTION

This invention relates to compositions and methods for the inhibition of expression of ras, a naturally occurring protein which occasionally converts to an activated form that has been implicated in tumor formation. Antisense oligonucleotides targeted to H-, Ki- and N-ras are provided. This invention is further directed to the detection of both normal and activated forms of the ras gene in cells and tissues, and can form the basis for research reagents and kits both for research and diagnosis. Furthermore, this invention is directed to prevention and treatment of conditions associated with ras.

BACKGROUND OF THE INVENTION

Alterations in the cellular genes which directly or indirectly control cell growth and differentiation are considered to be the main cause of cancer. There are some thirty families of genes, called oncogenes, which are implicated in human tumor formation. Members of one such family, the ras gene family, are frequently found to be mutated in human tumors. In their normal state, proteins produced by the ras genes are thought to be involved in normal cell growth and maturation. Mutation of the ras gene, causing an amino acid alteration at one of three critical positions in the protein product, results in conversion to a form which is implicated in tumor formation. A gene having such a mutation is said to be "mutant" or "activated." Unmutated ras is called "wild-type" or "normal" ras. It is thought that such a point mutation leading to ras activation can be induced by carcinogens or other environmental factors. Over 90% of pancreatic adenocarcinomas, about 50% of adenomas and adenocarcinomas of the colon, about 50% of adenocarcinomas of the lung and carcinomas of the thyroid, and a large fraction of malignancies of the blood such as acute myeloid leukemia and myelodysplastic syndrome have been found to contain activated ras oncogenes. Overall, some 10 to 20% of human tumors have a mutation in one of the three ras genes (H-ras, Ki-ras, or N-ras).

It is presently believed that inhibiting expression of activated oncogenes in a particular tumor cell might force the cell back into more normal growth. For example, Feramisco et al., Nature 1985, 314, 639–642, demonstrated that if cells transformed to a malignant state with an activated ras gene are microinjected with antibody which binds to the protein product of the ras gene, the cells slow their rate of proliferation and adopt a more normal appearance. This has been interpreted as support for the involvement of the product of the activated ras gene in the uncontrolled growth typical of cancer cells.

There is a great desire to provide compositions of matter which can modulate the expression of ras, and particularly to provide compositions of matter which specifically modulate the expression of activated ras. It is greatly desired to provide methods of diagnosis and detection of nucleic acids encoding ras in animals. It is also desired to provide methods of diagnosis and treatment of conditions arising from ras activation. In addition, improved research kits and reagents for detection and study of nucleic acids encoding ras are desired.

Inhibition of oncogene expression has been accomplished using retroviral vectors or plasmid vectors which express a 2-kilobase segment of the Ki-ras protooncogene RNA in antisense orientation. Mukhopadhyay, T. et al. (1991) Cancer Research 51, 1744–1748; PCT Patent Application PCT/US92/01852 (WO 92/15680); Georges, R. N. et al. (1993) Cancer Research, 53, 1743–1746.

Antisense oligonucleotide inhibition of oncogenes has proven to be a useful tool in understanding the roles of various oncogene families. Antisense oligonucleotides are small oligonucleotides which are complementary to the "sense" or coding strand of a given gene, and as a result are also complementary to, and thus able to stably and specifically hybridize with, the mRNA transcript of the gene. Holt et al., Mol. Cell Biol. 1988, 8, 963–973, have shown that antisense oligonucleotides hybridizing specifically with mRNA transcripts of the oncogene c-myc, when added to cultured-HL60 leukemic cells, inhibit proliferation and induce differentiation. Anfossi et al., Proc. Natl. Acad. Sci. 1989, 86, 3379–3383, have shown that antisense oligonucleotides specifically hybridizing with mRNA transcripts of the c-myb oncogene inhibit proliferation of human myeloid leukemia cell lines. Wickstrom et al., Proc. Nat. Acad. Sci. 1988, 85, 1028–1032, have shown that expression of the protein product of the c-myc oncogene as well as proliferation of HL60 cultured leukemic cells are inhibited by antisense oligonucleotides hybridizing specifically with c-myc mRNA. U.S. Pat. No: 4,871,838 (Bos et al.) discloses oligonucleotides complementary to a mutation in codon 13 of N-ras to detect said mutation. U.S. Pat. No: 4,871,838 (Bos et al.) discloses molecules useful as probes for detecting a mutation in DNA which encodes a ras protein.

In all these cases, instability of unmodified oligonucleotides has been a major problem, as they are subject to degradation by cellular enzymes. PCT/US88/01024 (Zon et al.) discloses phosphorothioate oligonucleotides hybridizable to the translation initiation region of the amplified c-myc oncogene to inhibit HL-60 leukemia cell growth and DNA synthesis in these cells. Tidd et al., Anti-Cancer Drug Design 1988, 3, 117–127, evaluated methylphosphonate antisense oligonucleotides hybridizing specifically to the activated N-ras oncogene and found that while they were resistant to biochemical degradation and were nontoxic in cultured human HT29 cells, they did not inhibit N-ras gene expression and had no effect on these cells. Chang et al. showed that both methylphosphonate and phosphorothioate oligonucleotides hybridizing specifically to mRNA transcripts of the mouse Balb-ras gene could inhibit translation of the protein product of this gene in vitro. Chang et al., Anti-Cancer Drug Design 1989, 4, 221–232; Brown et al., Oncogene Research 1989, 4, 243–252. It was noted that $T_m$ was not well correlated with antisense activity of these oligonucleotides against in vitro translation of the ras p21 protein product. Because the antisense oligonucleotides used by Chang et al. hybridize specifically with the translation initiation region of the ras gene, they are not expected to show any selectivity for activated ras and the binding ability of these oligonucleotides to normal (wild-type) vs. mutated (activated) ras genes was not compared.

Helene and co-workers have demonstrated selective inhibition of activated (codon 12 G→T transition) H-ras mRNA expression using a 9-mer phosphodiester linked to an acridine intercalating agent and/or a hydrophobic tail. This compound displayed selective targeting of mutant ras message in both Rnase H and cell proliferation assays at low micromolar concentrations. Saison-Behmoaras, T. et al., *EMBO J.* 1991, 10, 1111–1118. Chang and co-workers disclose selective targeting of mutant H-ras message; this time the target was H-ras codon 61 containing an A—T transversion and the oligonucleotide employed was either an 11-mer methylphosphonate or its psoralen derivative. These compounds, which required concentrations of 7.5–150 µM for activity, were shown by immunoprecipitation to selectively inhibit mutant H-ras p21 expression relative to normal p21. Chang et al., *Biochemistry* 1991, 30, 8283–8286.

SUMMARY OF THE INVENTION

The present invention relates to antisense LP oligonucleotides which are targeted to human ras, and methods of using them. More specifically, the present invention provides oligonucleotides which are targeted to mRNA encoding human H-ras, Ki-ras and N-ras and which are capable of inhibiting ras expression. Oligonucleotides targeted to a 5' untranslated region, translation initiation site, coding region or 3' untranslated region of human N-ras are provided. Methods of modulating ras expression, of inhibiting the proliferation of cancer cells and of treating conditions associated with ras are provided. These methods employ the oligonucleotides of the invention.

DETAILED DESCRIPTION OF THE INVENTION

Figure 1A:
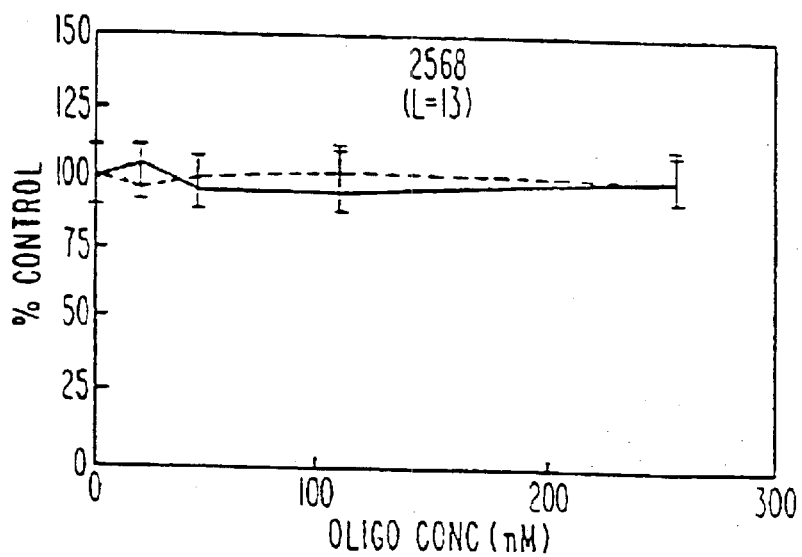
FIG. 1 is a series of 8 panels (FIGS. 1a–1h) showing inhibition of ras in a dose-dependent manner. Solid lines are activity against wild-type (normal) ras, dotted lines show activity against activated (mutant) ras.
Figure 1B:
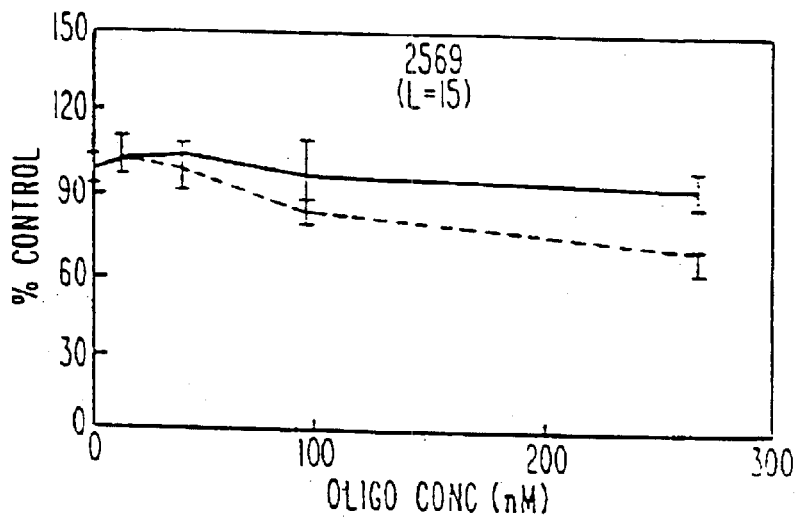
Figure 1C:
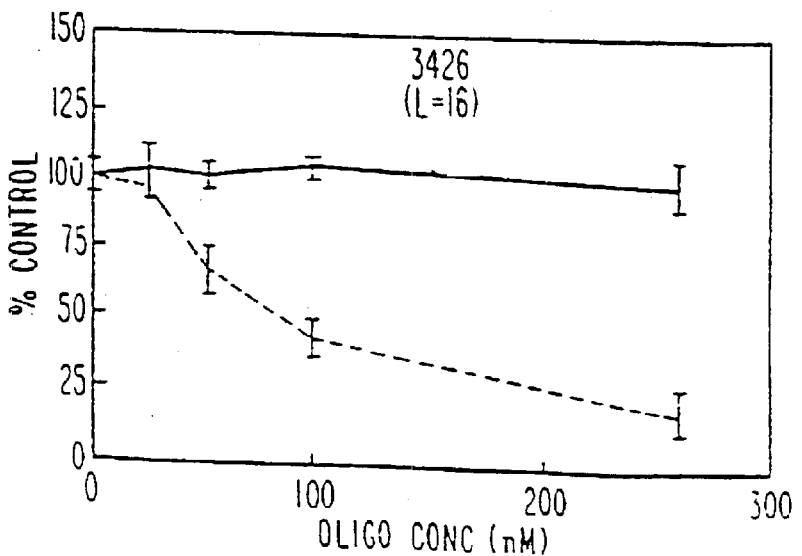
Figure 1D:
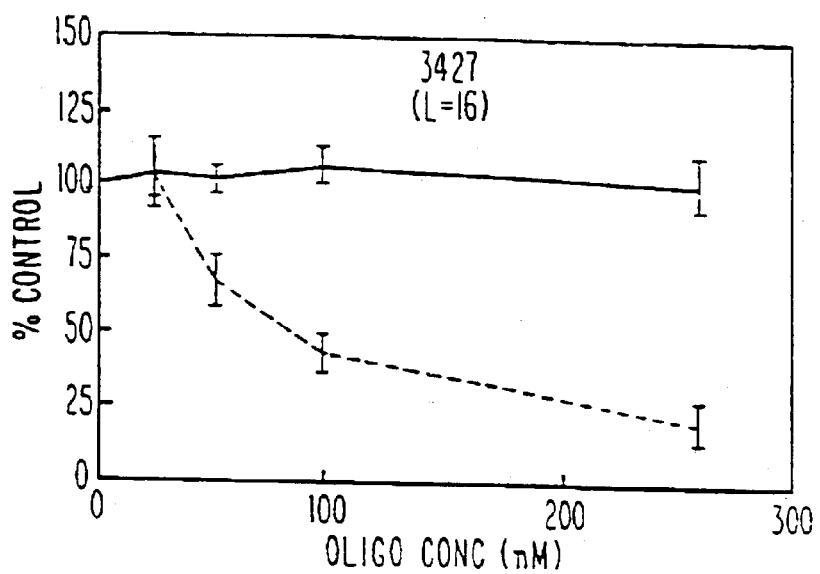
Figure 1E:
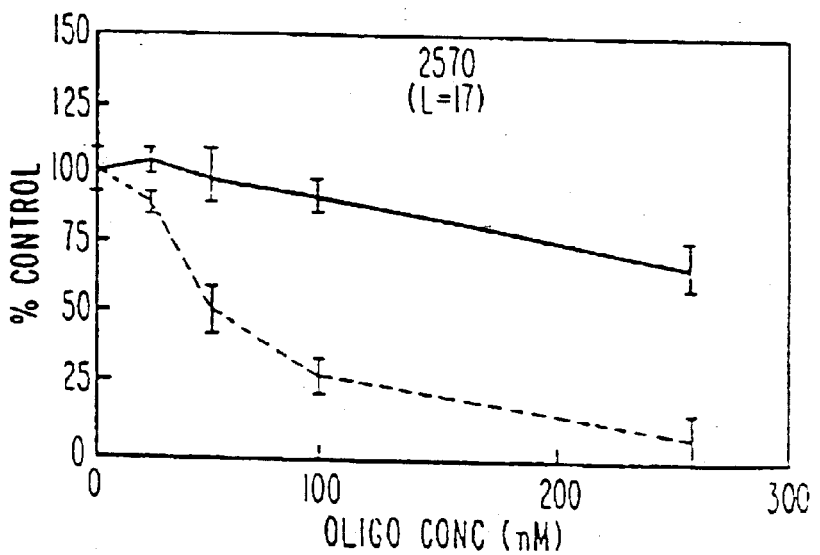
Figure 1F:
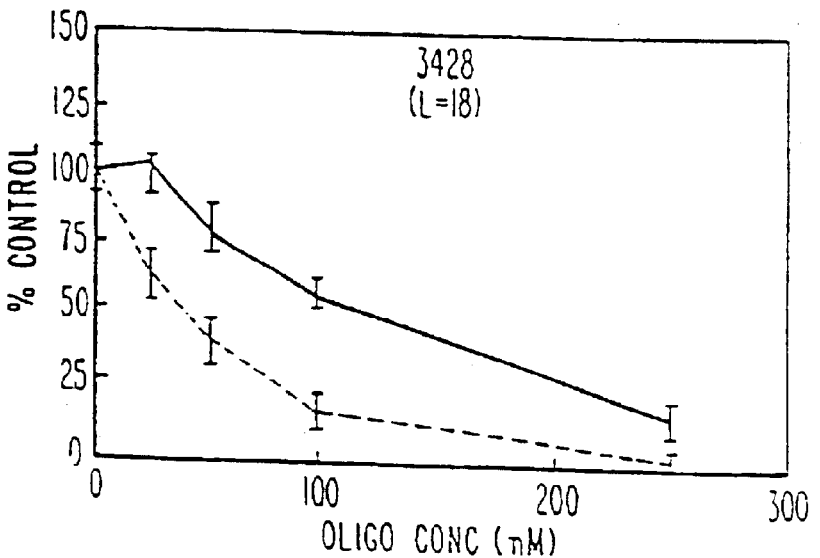
Figure 1G:
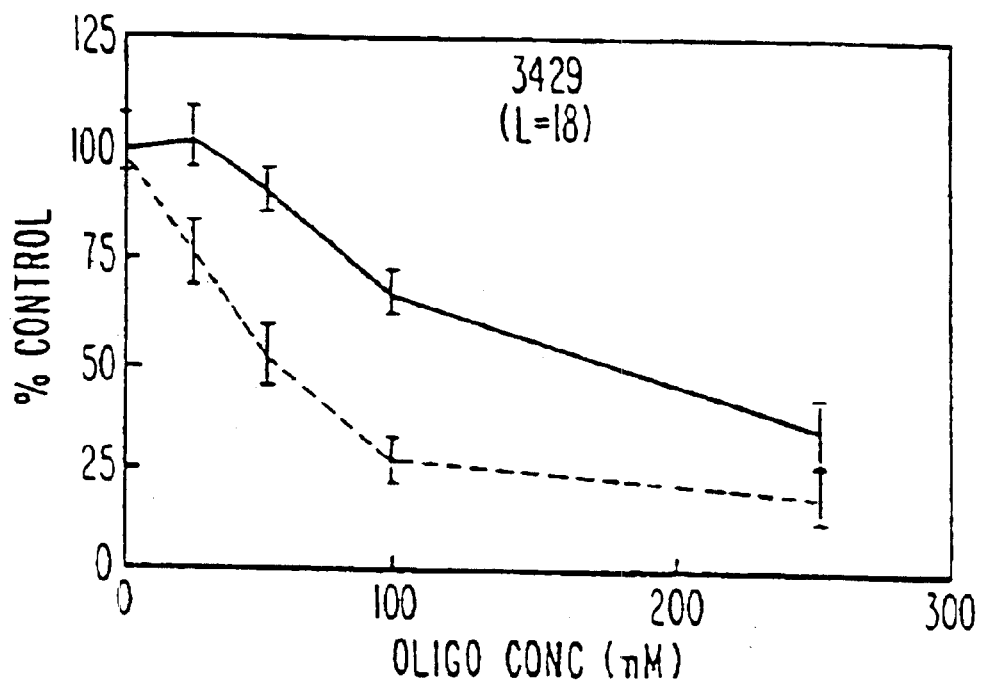
Figure 1H:
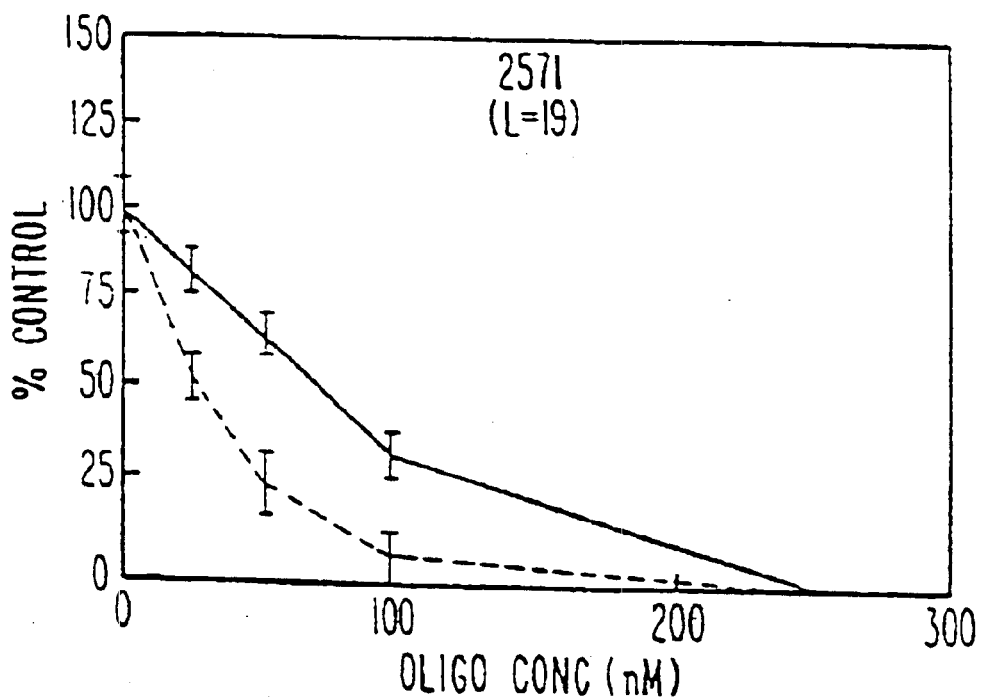

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. In addition, the ability to study cell transformation in carefully controlled, quantitative in vitro assays has led to the identification of specific genes capable of inducing the transformed cell phenotype. Such cancer-causing genes, or oncogenes, are believed to acquire transformation-inducing properties through mutations leading to changes in the regulation of expression of their protein products. In some cases such changes occur in non-coding DNA regulatory domains, such as promoters and enhancers, leading to alterations in the transcriptional activity of oncogenes, resulting in over- or under-expression of their gene products. In other cases, gene mutations occur within the coding regions of oncogenes, leading to the production of altered gene products that are inactive, overactive, or exhibit an activity that is different from the normal (wild-type) gene product.

To date, more than 30 cellular oncogene families have been identified. These genes can be categorized on the basis of both their subcellular location and the putative mechanism of action of their protein products. The ras oncogenes are members of a gene family which encode related proteins that are localized to the inner face of the plasma membrane. ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, Ki-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The sequences of H-ras, Ki-ras and N-ras are known. Capon et al., *Nature* 302 1983, 33–37; Kahn et al., *Anticancer Res.* 1987, 7, 639–652; Hall and Brown, *Nucleic Acids Res.* 1985, 13, 5255–5268. The most commonly detected activating ras mutation found in human tumors is in codon 12 of the H-ras gene in which a base change from GGC to GTC results in a glycine-to-valine substitution in the GTPase regulatory domain of the ras protein product. Tabin, C. J. et al., *Nature* 1982, 300, 143–149; Reddy, P. E. et al., Nature 1982, 300, 149–152; Taparowsky, E. et al., *Nature* 1982, 300, 762–765. This single amino acid change is thought to abolish normal control of ras protein function, thereby converting a normally regulated cell protein to one that is continuously active. It is believed that such deregulation of normal ras protein function is responsible for the transformation from normal to malignant growth. It is therefore believed that inhibition of ras expression is useful in treatment and/or prevention of malignant conditions, i.e., cancer and other hyperproliferative conditions.

The H-ras gene has recently been implicated in a serious cardiac arrhythmia called long Q-T syndrome, a hereditary condition which often causes sudden death if treatment is not given immediately. Frequently, there are no symptoms prior to the onset of the erratic heartbeat. Whether the H-ras gene, is precisely responsible for long Q-T syndrome is unclear. However, there is an extremely high correlation between inheritance of this syndrome and the presence of a particular variant of the chromosome 11 region surrounding the H-ras gene. Therefore, the H-ras gene is a useful indicator of increased risk of sudden cardiac death due to the long Q-T syndrome.

N-ras was first identified as an oncogene in gene transfer experiments. Hall et al. *Nature* 1983, 303: 396–400. Its activation was characterized by Taparowsky et al. *Cell* 1983 34: 581–6. Activated N-ras is found in many hematologic neoplasms and solid tumors, suggesting a role for N-ras in the development or maintenance of hyperproliferative conditions.

The present invention provides oligonucleotides for inhibition of human ras gene expression. Such oligonucleotides specifically hybridize with selected DNA or mRNA deriving from a human ras gene. The invention also provides oligonucleotides for selective inhibition of expression of the mutant form of ras. This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, for example, a cellular gene (or mRNA made from the gene) whose expression is associated with a particular disease state, or a foreign nucleic acid from an infectious agent. In the present invention, the target is a nucleic acid encoding ras; in other words, the ras gene or mRNA expressed from the ras gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of ras gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding H-ras, Ki-ras or N-ras. In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of the ras mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with ras protein expression.

The present invention provides oligonucleotides for modulation of ras gene expression. Such oligonucleotides are targeted to nucleic acids encoding ras. As hereinbefore defined, "modulation" means either inhibition or stimulation. Inhibition of ras gene expression is presently the preferred form of modulation.

In the context of this invention, the term "oligonucleotide" refers to an oligomer or polymer of nucleotide or nucleoside monomers consisting of naturally occurring bases, sugars and intersugar (backbone) linkages.

The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase ras mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance antisense oligonucleotide inhibition of ras gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. A discussion of antisense oligonucleotides and some desirable modifications can be found in De Mesmaeker et al. *Acc. Chem. Res.* 1995, 28:366–374.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH$,—$N(CH_3)$—O—$CH_2$ [known as a methylene (methylimino) or MMI backbone], $CH_2$—O—N ($CH_3$)—$CH_2$, $CH_2$—N ($CH_3$)—N ($CH_3$)—$CH_2$ and O—N ($CH_3$)—$CH_2$—$CH_2$ backbones, wherein the native phosphodiester backbone is represented as O—P—O—$CH$,). The amide backbones disclosed by De Mesmaeker et al. *Acc. Chem. Res.* 1995, 28:366–374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-$CH_2CH_2OCH_3$, also known as 2'-O-(2-methoxyethyl)] (Martin et al., *Helv. Chim. Acta,* 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2' deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Kornberg, A., *DNA Replication,* W. H. Freeman & Co., San Francisco, 1980, pp75–77; Gebeyehu, G., et al. *Nucl. Acids Res.* 1987, 15:4513). A "universal" base known in the art, e.g., inosine, may be included. 5-me-C substitutions have been shown to increase nucleic acid duplex stability by 0.6–1.2° C. (Sanghvi, Y. S., in Crooke, S. T. and Lebleu, B., eds., *Antisense Research and Applications,* CRC Press, Boca Raton, 1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling VA) to synthesize fluorescently labeled, biotinylated or other modified oligonucleotides such as cholesterol-modified oligonucleotides.

The oligonucleotides in accordance with this invention preferably comprise from about 8 to about 50 nucleic acid base units. In the context of this invention it is understood that this encompasses non-naturally occurring oligomers as hereinbefore described, having 8 to 50 monomers.

The oligonucleotides of this invention can be used in diagnostics, therapeutics and as research reagents and kits. Since the oligonucleotides of this invention hybridize to the ras gene, sandwich and other assays can easily be constructed to exploit this fact. Furthermore, since the oligonucleotides of this invention hybridize preferentially to the mutant (activated) form of the ras oncogene, such assays can be devised for screening of cells and tissues for ras conversion from wild-type to activated form. Such assays can be utilized for differential diagnosis of morphologically similar tumors, and for detection of increased risk of cancer stemming from ras gene activation. Provision of means for detecting hybridization of oligonucleotide with the ras gene can routinely be accomplished. Such provision may include enzyme conjugation, radiolabelling or any other suitable detection systems. Kits for detecting the presence or absence of nucleic acids encoding ras or activated ras may also be prepared.

The following specific descriptions serve to illustrate the invention and are not intended to limit the scope of the invention:

Antisense Oligonucleotide Inhibition of ras-Luciferase Gene Expression: A series of antisense phosphorothioate oligonucleotides targeted to either the H-ras translation initiation codon or the codon-12 point mutation of activated H-ras were screened using the ras-luciferase reporter gene system described in Examples 2–5. Of this initial series, six oligonucleotides were identified that gave significant and reproducible inhibition of ras-luciferase activity. The base sequences, sequence reference numbers and SEQ ID numbers of these oligonucleotides (all are phosphorothioates) are shown in Table 1.

TABLE 1

| OLIGO | SEQUENCE | SEQ ID NO: |
|---|---|---|
| 2502 | CTT-ATA-TTC-CGT-CAT-CGC-TC | 1 |
| 2503 | TCC-GTC-ATC-GCT-CCT-CAG-GG | 2 |
| 2570 | CCA-CAC-CGA-CGG-CGC-CC | 3 |
| 2571 | CCC-ACA-CCG-ACG-GCG-CCC-A | 4 |
| 2566 | GCC-CAC-ACC-GAC-GGC-GCC-CAC | 5 |
| 2560 | TGC-CCA-CAC-CGA-CGG-CGC-CCA-CC | 6 |

A dose-response experiment was performed in which cells expressing either the normal ras-luciferase reporter gene or the mutant ras-luciferase reporter gene were treated with increasing concentrations of the phosphorothioate oligonucleotide 2503 (SEQ ID NO: 2). This compound is targeted to the translational initiation codon of H-ras RNA transcripts. Treatment of cells with this oligonucleotide resulted in a dose-dependent inhibition of ras-luciferase activity, displaying IC50 values of approximately 50 nM for both the normal and the mutant ras targets. The observation that an oligonucleotide targeted to the ras translation initiation codon is equally effective in reducing both mutant and normal ras expression is expected since the two targets have identical sequence compositions in the region surrounding the AUG translation initiation site.

Another dose-response experiment was performed in which cells were treated with phosphorothioate oligonucleotide 2570 (SEQ ID NO: 3), a compound that is targeted to the codon-12 point mutation of mutant (activated) H-ras RNA. Treatment of cells with increasing concentrations of this oligonucleotide resulted in a dose-dependent inhibition of ras-luciferase activity in cells expressing either the mutant form or the normal form of ras-luciferase. However, oligonucleotide 2570 displayed approximately threefold selectivity toward the mutant form of ras-luciferase as compared to the normal form. In fact, 2570 displayed an IC50 value for the mutant form of ras-luciferase of approximately 100 nM whereas the same compound displayed in IC50 value of approximately 250 nM for the unmutated form.

Cells expressing either the normal form or the mutant form of ras-luciferase were treated with a single dose (0.5μM) of oligonucleotide targeted to either the translation initiation codon of H-ras or the codon-12 point mutation. The antisense phosphorothioate oligonucleotides tested are shown in Table 1. Compound 2503 (SEQ ID NO: 2), targeted to the ras translational initiation codon, was most effective in inhibiting ras-luciferase activity, giving approximately 80%. inhibition of both normal and mutant targets. ISIS 2502 gave 30–35% inhibition of both targets. Of the three compounds targeted to the codon-12 point mutation of activated H-ras, only the 17-mer oligonucleotide 2570 (SEQ ID NO: 3) displayed selectivity toward the mutated form of ras-luciferase as compared to the normal form, giving approximately 22% inhibition of the normal target and 68% inhibition of the mutant target. ISIS 2571 gave approximately 60% inhibition of both targets and ISIS 2566 gave 65–70% inhibition of both targets. Table 2 summarizes data obtained with all 13 antisense oligonucleotides targeted to H-ras. A scrambled control oligonucleotide gave no inhibition of either mutant or normal ras and a control oligonucleotide (ISIS 2907; SEQ ID NO: 19) complementary to the codon-12 region of normal ras gave 70% inhibition of the normal target but had no effect on the mutant ras. Shown for each oligonucleotide is its sequence, region to which it is complementary, and its activity in suppressing expression of the ras-luciferase fusion protein (given as IC50, the concentration in nM necessary to give 50% inhibition of ras-luciferase expression). The longer phosphorothioates targeted to the codon-12 point mutation, while displaying substantial antisense activity toward ras-luciferase expression, did not demonstrate selective inhibition of expression of the mutant form of ras-luciferase. Phosphorothioate oligonucleotides targeted to the codon-12 point mutation that were less than 17 nucleotides in length did not show activity to either form of ras-luciferase. These results demonstrate effective antisense activity of phosphorothioate oligonucleotides targeted to ras sequences.

Antisense oligonucleotides specifically hybridizable with the H-ras AUG- Three 20-base phosphorothioate oligonucleotides, targeted to the H-ras AUG codon, were compared for their ability to inhibit ras-luciferase expression in transient transfection assays as described in Examples 2–5. These oligonucleotides, ISIS 2502 (SEQ ID NO: 1), 2503 (SEQ ID NO: 2) and 6186 (SEQ ID NO: 7) shown in Table 2, were tested for inhibition of ras-luciferase expression at a single dose (100 nM) in HeLa cells. All three AUG-targeted oligonucleotides were effective in inhibiting ras-luciferase expression. These three phosphorothioate oligonucleotides were also prepared with a 2'-O-methyl modification on each sugar. The 2'-O-methylated version of ISIS 2503 (SEQ ID NO: 2) also inhibited ras-luciferase expression with an. IC50 between 200 and 500 nM. SEQ ID NO: 7 as a 2'-O-methyl gave approximately 40% inhibition at the highest dose (500 nM).

TABLE 2

Antisense oligonucleotides targeted to mutant H-ras
(Oligonucleotide sequences shown 5' to 3')

| ISIS # | TARGET | SEQUENCE | IC50 (nM) | SEQ. ID NO. |
|---|---|---|---|---|
| 2502 | AUG | CTTATATTCCGTCATCGCTC | 750 | 1 |
| 2503 | AUG | TCCGTCATCGCTCCTCAGGG | 50 | 2 |
| 6186 | AUG | TATTCCGTCATCGCTCCTCA | — | 7 |
| 2563 | CODON 12 | CGACG | — | 8 |
| 2564 | CODON 12 | CCGACGG | — | 9 |
| 2565 | CODON 12 | ACCGACGGC | — | 10 |
| 2567 | CODON 12 | CACCGACGGCG | — | 11 |
| 2568 | CODON 12 | ACACCGACGGCGC | — | 12 |
| 2569 | CODON 12 | CACACCGACGGCGCC | — | 13 |
| 3426 | CODON 12 | CCACACCGACGGCGCC | — | 14 |
| 3427 | CODON 12 | CACACCGACGGCGCCC | — | 15 |
| 2570 | CODON 12 | CCACACCGACGGCGCCC | 100 | 3 |
| 3428 | CODON 12 | CCCACACCGACGGCGCCC | — | 16 |
| 3429 | CODON 12 | CCACACCGACGGCGCCCA | — | 17 |
| 2571 | CODON 12 | CCCACACCGACGGCGCCCA | 250 | 4 |
| 2566 | CODON 12 | GCCCACACCGACGGCGCCCAC | 250 | 5 |
| 2560 | CODON 12 | TGCCCACACCGACGGCGCCCACC | 750 | 6 |
| 2561 | CODON 12 | TTGCCCACACCGACGGCGCCCACCA | 1000 | 18 |
| 2907 | CODON 12 (normal) | CCACACCGCCGGCGCCC | — | 19 |

Oligonucleotide length affects antisense activity and specificity: Oligonucleotides targeted to the H-ras codon-12 mutation also were effective in inhibiting expression of ras-luciferase. A series of eleven phosphorothioate oligonucleotides, ranging in length between 5 and 25 bases, were made and tested for ability to inhibit mutant and wild type ras-luciferase in transient transfection assays as described in Examples 2–5. The oligonucleotides are shown in Table 2. At 100 nM oligonucleotide concentration, oligonucleotides 15 bases or greater in length were found to inhibit expression of the mutant H-ras target. Selective inhibition of mutant over wild type ras-luciferase expression was observed for oligonucleotides between 15 and 19 bases in length. The maximum selectivity observed for inhibition of mutant ras-luciferase relative to wild type was for the 17-mer 2570 (SEQ ID NO: 3) and was approximately 4-fold. In order to demonstrate that 2570 was acting in a sequence-specific manner, a variant of this compound was tested (2907; SEQ ID NO: 19) in which the central adenosine residue was replaced with cytosine, making this oligonucleotide perfectly complementary to the normal H-ras target. Hence, this oligonucleotide will contain a single mismatch at the center of the oligonucleotide/RNA duplex when fully hybridized to the mutant H-ras sequence. Oligonucleotide 2907 selectively inhibited expression of normal ras-luciferase (88% inhibition) relative to mutant ras-luciferase (5% inhibition).

Two 16-mers and two 18-mers complementary to the mutant codon-12 region (Table 2) were tested as described in Examples 2–5. FIG. 1 shows the results of an experiment in which antisense activity and mutant selectivity was determined for oligonucleotides of length 13, 15, 16, 17, 18 and 19 bases in a dose-dependent manner. The results obtained with these oligonucleotides demonstrated that the compounds that were active against mutant H-ras sequences also showed selectivity; oligonucleotides of length 16 (SEQ ID NO: 14 and SEQ ID NO: 15) and 17 bases (SEQ ID NO: 3) displayed the greatest selectivity (4- and 5-fold, respectively). The 13 base compound, 2568 (SEQ ID:NO: 12), did not display antisense activity at any of the tested concentrations.

Chimeric 2'-O-methyl oligonucleotides with deoxy gaps: Based on the sequence of the mutant-selective 17-mer (2570), a series of chimeric phosphorothioate 2'-O-methyl oligonucleotides were synthesized in which the end regions consisted of 2'-O-methyl nucleosides and the central residues formed a "deoxy gap". The number of deoxy residues ranged from zero (full 2'-O-methyl) to 17 (full deoxy). These oligonucleotides are shown in Table 3.

TABLE 3

Chimeric phosphorothioate oligonucleotides having 2'-O-methyl ends (bold) and central deoxy gap (Mutant codon-12 target)

| OLIGO | # DEOXY | SEQUENCE | SEQ ID NO: |
|---|---|---|---|
| 4122 | 0 | CCACACCGACGGCGCCC | 3 |
| 3975 | 1 | CCACACCGACGGCGCCC | 3 |
| 3979 | 3 | CCACACCGACGGCGCCC | 3 |
| 4236 | 4 | CCACACCGACGGCGCCC | 3 |
| 4242 | 4 | CCACACCGACGGCGCCC | 3 |
| 3980 | 5 | CCACACCGACGGCGCCC | 3 |
| 3985 | 7 | CCACACCGACGGCGCCC | 3 |
| 3984 | 9 | CCACACCGACGGCGCCC | 3 |
| 2570 | 17 | CCACACCGACGGCGCCC | 3 |

These oligonucleotides were characterized for hybridization efficiency as described in Example 6, ability to direct RNase H cleavage in vitro using mammalian RNase H as described in Example 8, and for antisense activity. Antisense activity against full length H-ras mRNA was determined using a transient co-transfection reporter gene system in which H-ras gene expression was monitored using a ras-responsive enhancer element linked to the reporter gene luciferase, as described in Example 9.

Antisense activity of deoxy-gapped oligonucleotides against full length ras mRNA: The beneficial properties of enhanced target affinity conferred by 2'-O-methyl modifications can be exploited for antisense inhibition provided these compounds are equipped with RNase H-sensitive deoxy gaps of the appropriate length. 2'-O-methyl deoxy gap oligonucleotides were tested for antisense activity against the full length H-ras mRNA using the H-ras transactivation reporter gene system described in Example 9. Antisense experiments were performed initially at a single oligonucleotide concentration (100 nM). Chimeric 2'-O-methyl oligonucleotides containing deoxy gaps of five or more residues inhibited H-ras gene expression. The full deoxy compound gave approximately 50% inhibition. The fully 2'-O-methyl, 1-deoxy and 3-deoxy gave no inhibition. The 5-deoxy, 7-deoxy and 9-deoxy compounds gave approximately 85%, 95% and 90% inhibition, respectively. These compounds displayed activities greater than that of the full deoxy parent compound.

Dose response experiments were performed using these active compounds, along with the 2'-O-methyl chimeras containing four deoxy residues. Oligonucleotide-mediated inhibition of full-length H-ras by these oligonucleotides was dose-dependent. The most active compound was the seven-residue deoxy chimera, which displayed an activity approximately five times greater than that of the full deoxy oligonucleotide.

Figure 2:
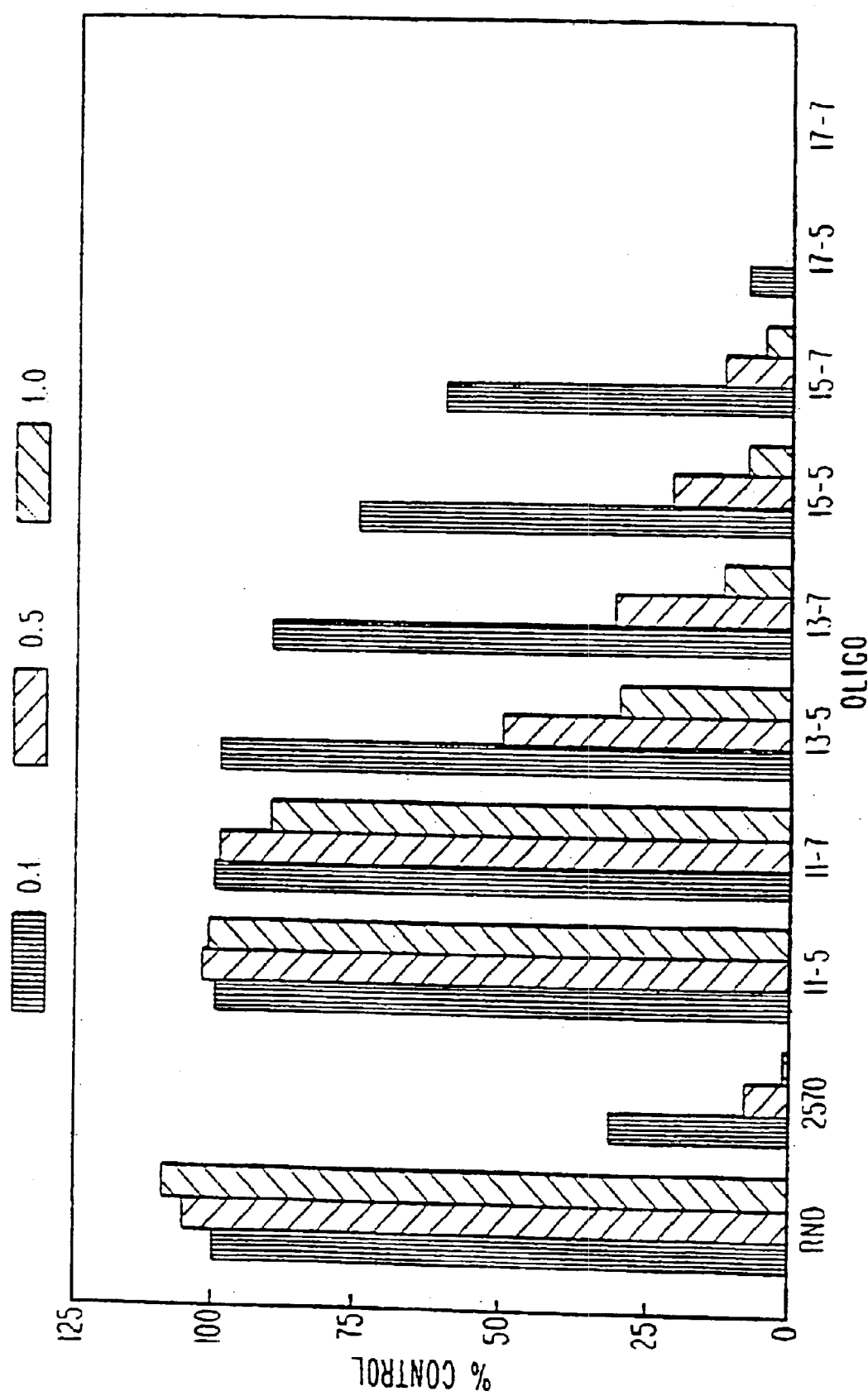
FIG. 2 is a bar graph showing antisense activities of a uniform deoxy phosphorothioate and shortened chimeric oligonucleotides against ras-luciferase.

Shortened chimeric oligonucleotides: Enhanced target affinity conferred by the 2'-O-methyl modifications was found to confer activity on short chimeric oligonucleotides. A series of short 2'-O-methyl chimeric oligonucleotides were tested for $T_m$ and antisense activity vs. full length. ras as described in Example 9. Table 4 shows $T_{ms}$ for oligonucleotides 11, 13, 15 and 17 nucleotides in length, having deoxy gaps either 5 bases long or 7 bases long. In sharp contrast to the full deoxy 13-mer, both 2'-O-methyl chimeric 13-mers inhibited ras expression, and one of the 11-mers was also active. This is shown in FIG. 2.

TABLE 4

| LENGTH | $T_m$ (° C.) | SEQUENCE | SEQ ID NO: |
|---|---|---|---|
| 17 | 77.2 | CCACACCGACGGCGCCC | 3 |
| 15 | 69.8 | CACACCGACGGCGCC | 13 |
| 13 | 62.1 | ACACCGACGGCGC | 12 |
| 11 | 47.3 | CACCGACGGCG | 11 |
| 17 | 74.6 | CCACACCGACGGCGCCC | 3 |
| 15 | 66.2 | CACACCGACGGCGCC | 13 |
| 13 | 58.0 | ACACCGACGGCGC | 12 |
| 11 | 27.7 | CACCGACGGCG | 11 |

Figure 3:
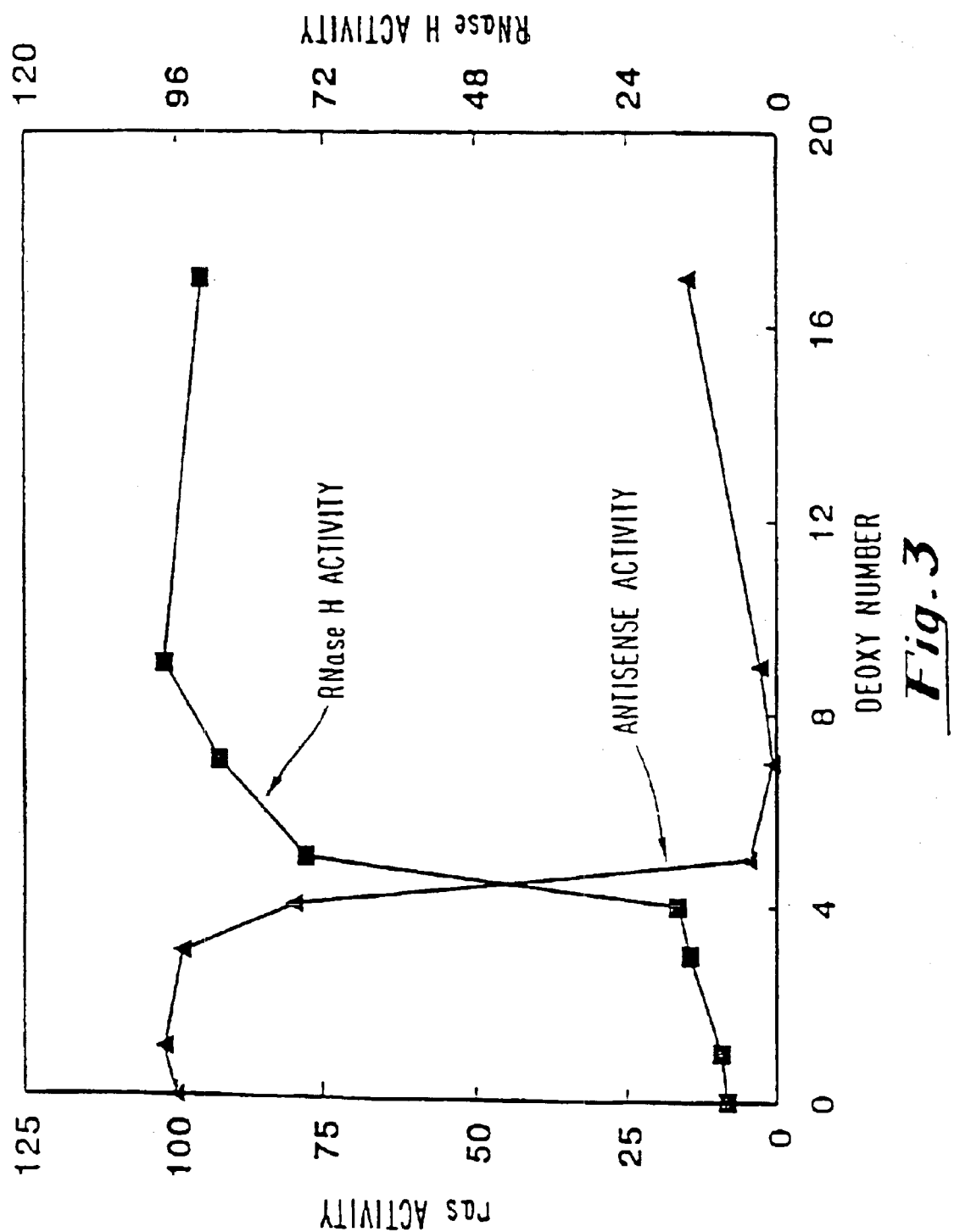
FIG. 3 is a line graph showing correlation between antisense activity and ability to activate RNAse H as a function of deoxy gap length using phosphorothioate 2'-O-methyl oligonucleotides targeted against ras.

Relative antisense activity and ability to activate RNase H cleavage in vitro by chimeric 2'-O-methyl oligonucleotides is well correlated with deoxy length (FIG. 3).

Asymmetrical deoxy gaps: It is not necessary that the deoxy gap be in the center of the chimeric molecule. It was found that chimeric molecules having the nucleotides of the region at one end modified at the 2' position to enhance binding and the remainder of the molecule unmodified (2' deoxy) can still inhibit ras expression. Oligonucleotides of SEQ ID NO: 3 (17-mer complementary to mutant codon 12) in which a 7-deoxy gap was located at either the 5' or 3' side of the 17-mer, or at different sites within the middle of the molecule, all demonstrated RNase H activation and antisense activity. However, a 5-base gap was found to be more sensitive to placement, as some gap positions rendered the duplex a poor activator of RNase H: and a poor antisense inhibitor. Therefore, a 7-base deoxy gap is preferred.

Other sugar modifications: The effects of other 2' sugar modifications besides 2'-O-methyl on antisense activity in chimeric oligonucleotides have been examined. These modifications are listed in Table 5, along with the $T_m$ values obtained when 17-mer oligonucleotides having 2'-modified nucleotides flanking a 7-base deoxy gap were hybridized with a 25-mer oligoribonucleotide complement as described in Example 6. A relationship was observed for these oligonucleotides between alkyl length at the 2' position and $T_m$. As alkyl length increased, $T_m$, decreased. The 2'-fluoro chimeric oligonucleotide displayed the highest $T_m$ of the series.

TABLE 5

Correlation of $T_m$ with Antisense Activity
2'-modified 17-mer with 7-deoxy gap
CCACACCGACGGCGCCC (SEQ ID NO: 3)

| 2' MODIFICATION | $T_m$ (° C.) | IC50 (nM) |
| --- | --- | --- |
| Deoxy | 64.2 | 150 |
| O-Pentyl | 68.5 | 150 |
| O-Propyl | 70.4 | 70 |
| O-Methyl | 74.7 | 20 |
| Fluoro | 76.9 | 10 |

These 2' modified oligonucleotides were tested for antisense activity against H-ras using the transactivation reporter gene assay described in Example 9. As shown in Table 5, all of these 2' modified chimeric compounds inhibited ras expression, with the 2'-fluoro 7-deoxy-gap compound the most active. A 2'-fluoro chimeric oligonucleotide with a centered 5-deoxy gap was also active.

Chimeric phosphorothioate oligonucleotides having SEQ ID NO: 3 having 2'-O-propyl regions surrounding a 5-base or 7-base deoxy gap were compared to 2'-O-methyl chimeric oligonucleotides. ras expression in T24 cells was inhibited by both 2'-O-methyl and 2'-O-propyl chimeric oligonucleotides with a 7-deoxy gap and a uniform phosphorothioate backbone. When the deoxy gap was decreased to five nucleotides, only the 2'-O-methyl oligonucleotide inhibited ras expression.

Antisense oligonucleotide inhibition of H-ras gene expression in cancer cells: Two phosphorothioate oligonucleotides (2502, 2503) complementary to the ras AUG region were tested as described in Example 10, along with chimeric oligonucleotides (4998, 5122) having the same sequence and 7-base deoxy gaps flanked by 2'-O-methyl regions. These chimeric oligonucleotides are shown in Table 6.

TABLE 6

Chimeric phosphorothioate oligonucleotides
having 2'-O-methyl ends (bold) and central deoxy gap
(AUG target)

| OLIGO | # DEOXY | SEQUENCE | SEQ ID NO: |
| --- | --- | --- | --- |
| 2502 | 20 | CTTATATTCCGTCATCGCTC | 1 |
| 4998 | 7 | CTTATATTCCGTCATCGCTC | 1 |
| 2503 | 20 | TCCGTCATCGCTCCTCAGGG | 2 |
| 5122 | 7 | TCCGTCATCGCTCCTCAGGG | 2 |

Compound 2503 inhibited ras expression in T24 cells by 71%, and the chimeric compound (4998) inhibited ras mRNA even further (84% inhibition). Compound 2502, also complementary to the AUG region, decreased ras RNA levels by 26% and the chimeric version of this oligonucleotide (5122) demonstrated 15% inhibition. Also included in this assay were two oligonucleotides targeted to the mutant codon 12. Compound 2570 (SEQ ID NO: 3) decreased ras RNA by 82% and the 21 O-methyl chimeric version of this oligonucleotide with a seven -deoxy gap (3985) decreased ras RNA by 95%.

Oligonucleotides 2570 and 2503 were also tested to determine their effects on ras expression in HeLa cells, which have a wild-type (i.e., not activated) H-ras codon 12. While both of these oligonucleotides inhibited ras expression in T24 cells (having activated codon 12), only the oligonucleotide (2503) specifically hybridizable with the ras AUG inhibited ras expression in HeLa cells. Oligonucleotide 2570 (SEQ ID NO: 3), specifically hybridizable with the activated codon 12, did not inhibit ras expression in HeLa cells, because these cells lack the activated codon-12 target.

oligonucleotide 2570, a 17-mer phosphorothioate oligonucleotide complementary to the codon 12 region of activated H-ras, was tested for inhibition of ras expression (as described in Example 10) in T24 cells along with chimeric phosphorothioate 2'-O-methyl oligonucleotides 3980, 3985 and 3984, which have the same sequence as 2570 and have deoxy gaps of 5, 7 and 9 bases, respectively (shown in Table 3). The fully 2'-deoxy oligonucleotide 2570 and the three chimeric oligonucleotides decreased ras mRNA levels in T24 cells. Compounds 3985 (7-deoxy gap) and 3984 (9-deoxy gap) decreased ras mRNA by 81%; compound 3980 (5-deoxy gap) decreased ras mRNA by 61%. Chimeric oligonucleotides having this sequence, but having 2'-fluoro-modified nucleotides flanking a 5-deoxy (4689) or 7-deoxy (4690) gap, inhibited ras mRNA expression in T24 cells, with the 7-deoxy gap being preferred (82% inhibition, vs 63% inhibition for the 2'-fluoro chimera with a 5-deoxy gap).

Antisense oligonucleotide inhibition of proliferation of cancer cells: Three 17-mer oligonucleotides having the same sequence (SEQ ID NO: 3), complementary to the codon 12 region of activated ras, were tested for effects on T24 cancer cell proliferation as described in Example 11. 3985 has a 7-deoxy gap flanked by 2'-O-methyl nucleotides, and 4690 has a 7-deoxy gap flanked by 2'-F nucleotides (all are phosphorothioates). Effects of these oligonucleotides on cancer cell proliferation correlated well with their effects on ras mRNA expression shown by Northern blot analysis: oligonucleotide 2570 inhibited cell proliferation by 61%, the 2'-O-methyl chimeric oligonucleotide 3985 inhibited cell proliferation by 82%, and the 2'-fluoro chimeric analog inhibited cell proliferation by 93%.

In dose-response studies of these oligonucleotides on cell proliferation, the inhibition was shown to be dose-dependent in the 25 nM–100 nM range. IC50 values of 44 nM, 61 nM and 98 nM could be assigned to oligonucleotides 4690, 3985 and 2570, respectively. The random oligonucleotide control had no effect at the doses tested.

The effect of ISIS 2570 on cell proliferation was cell type-specific. The inhibition of T24 cell proliferation by this oligonucleotide was four times as severe as the inhibition of HeLa cells by the same oligonucleotide (100 nM oligonucleotide concentration). ISIS 2570 is targeted to the activated (mutant) ras codon 12, which is present in T24 but lacking in HeLa cells, which have the wild-type codon 12.

Chimeric backbone-modified oligonucleotides: Oligonucleotides discussed in previous examples have had uniform phosphorothioate backbones. The 2' modified chimeric oligonucleotides discussed above are not active in uniform phosphodiester backbones. A chimeric oligonucleotide was synthesized (ISIS 4226) having 2'-O-methyl regions flanking a 5-nucleotide deoxy gap, with the gap region having a P=S backbone and the flanking regions having a P=O backbone. Another chimeric oligonucleotide (ISIS 4223) having a P=O backbone in the gap and P=S in flanking regions was also made. These oligonucleotides are shown in Table 7.

Additional oligonucleotides were synthesized, completely 2' deoxy and having phosphorothioate backbones containing either a single phosphodiester (ISIS 4248), two phosphodiesters (ISIS 4546), three phosphodiesters (ISIS 4551), four phosphodiesters (ISIS 4593), five phosphodiesters (ISIS 4606) or ten phosphodiester linkages (ISIS-4241) in the center of the molecule. These oligonucleotides are also shown in Table 7.

TABLE 7

Chimeric backbone (P=S/P=O) oligonucleotides having 2'-O-methyl ends (bold) and central deoxy gap (backbone linkages indicated by s (P=S) or o (P=O)) Mutant codon-12 target

| OLIGO | P=S | SEQUENCE | SEQ ID NO: |
|---|---|---|---|
| 2570 | 16 | CsCsAsCsAsCsCsGsAsCsGsGsCsGsCsCsC | 3 |
| 4226 | 5 | CoCoAoCoAoCsGsAsCsGoGoCoGoCoCoC | 3 |
| 4233 | 11 | CsCsAsCsAsCoCoGoAoCoGsGsCsGsCsCsC | 3 |
| 4248 | 15 | CsCsAsCsAsCsCsGsAoCsGsGsCsGsCsCsC | 3 |
| 4546 | 14 | CsCsAsCsAsCsCsGoAoCsGsGsCsGsCsCsC | 3 |
| 4551 | 13 | CsCsAsCsAsCsCsGoAoCoGsGsCsGsCsCsC | 3 |
| 4593 | 12 | CsCsAsCsAsCsCoGoAoCoGsGsCsGsCsCsC | 3 |
| 4606 | 11 | CsCsAsCsAsCsCoGoAoCoGoGsCsGsCsCsC | 3 |
| 4241 | 6 | CsCsAsCoAoCoCoGoAoCoGoGoCoGsCsCsC | 3 |

Oligonucleotides were incubated in crude HeLa cellular extracts at 37° C. to determine their sensitivity to nuclease degradation as described in Dignam et al., *Nucleic Acids Res.* 1983, 11, 1475–1489. The oligonucleotide (4233) with a five-diester gap between phosphorothioate/2'-O-methyl wings had a $T_{1/2}$ of 7 hr. The oligonucleotide with a five-phosphorothioate gap in a phosphorothioate/2'-O-methyl molecule had a $T_{1/2}$ of 30 hours. In the set of oligonucleotides having one to ten diester linkages, the oligonucleotide (4248) with a single phosphodiester linkage was as stable to nucleases as was the full-phosphorothioate molecule, ISIS 2570, showing no degradation after 5 hours in HeLa cell extract. Oligonucleotides with two-, three- and four-diester gaps had $T_{1/2}$ of approximately 5.5 hours, 3.75 hours, and 3.2 hours, and oligonucleotides with five or ten deoxy linkages had $T_{1/2}$ of 1.75 hours and 0.9 hours, respectively.

Antisense activity of chimeric backbone-modified oligonucleotides: A uniform phosphorothioate backbone is not required for antisense activity. ISIS 4226 and ISIS 4233 were tested in the ras-luciferase reporter system for effect on ras expression as described in Examples 2–5, along with ISIS 2570 (fully phosphorothioate/all deoxy), ISIS 3980 (fully phosphorothioate, 2-O-methyl wings with deoxy gap) and ISIS 3961 (fully phosphodiester, 2'-O-methyl wings with deoxy gap). All of the oligonucleotides having a P=S (i.e., nuclease-resistant) gap region inhibited ras expression. The two completely 2' deoxy oligonucleotides having phosphorothioate backbones containing either a single phosphodiester (ISIS 4248) or ten phosphodiester linkages (ISIS 4241) in the center of the molecule were also assayed for activity. The compound containing a single P=O was just as active as a full P=S molecule, while the same compound containing ten P=O was completely inactive.

Chimeric phosphorothioate oligonucleotides of SEQ ID NO: 3 were made, having a phosphorothioate backbone in the 7-base deoxy gap region only, and phosphodiester in the flanking regions, which were either 2'-O-methyl or 2-O-propyl. The oligonucleotide with the 2-O-propyl diester flanking regions was able to inhibit ras expression.

Inhibition of ras-luciferase gene expression by antisense oligonucleotides containing modified bases: A series of antisense phosphorothioate oligonucleotides complementary to the codon-12 point mutation of activated ras were synthesized as described, having a 2-(amino)adenine at the position complementary to the uracil of the mutated codon 12. Because the amino group at the 2-position of the adenine is able to hydrogen bond with the oxygen in the 2-position on the uracil, three hydrogen bonds instead of the usual two are formed. This serves to greatly stabilize the hybridization of the 2-(amino)adenine-modified antisense oligonucleotide to the activated ras gene, while destabilizing or having no net effect on the stability of this oligonucleotide to the wild-type codon 12, because of the modified A-G mismatch at this position. This increases the specificity of the modified oligonucleotide for the desired target.

An oligonucleotide having a single 2,6-(diamino) adenosine at this position in an otherwise unmodified uniform phosphorothioate 17-mer (sequence identical to 2570, SEQ ID NO: 3) was found to be at least as effective an RNase H substrate as the 2570 sequence. It is therefore expected to be an effective antisense molecule. An oligonucleotide having a single 2,-(diamino)adenosine at this position in a deoxy gapped phosphorothioate oligonucleotide of the same sequence also demonstrates RNase H activation.

In vivo anti-tumor data: ISIS 2503 (SEQ ID NO: 2) has been evaluated for activity against human tumors in vivo as described in Examples 14 and 15. These studies employed a human lung adenocarcinoma cell line (A549) which was subcutaneously implanted into nude mice, resulting in tumor growth at site of implantation. Since these cells do not contain a mutation in the H-ras gene, but do express normal H-ras, only the AUG-directed oligonucleotide ISIS 2503 was evaluated for anti-tumor activity.

Figure 4:
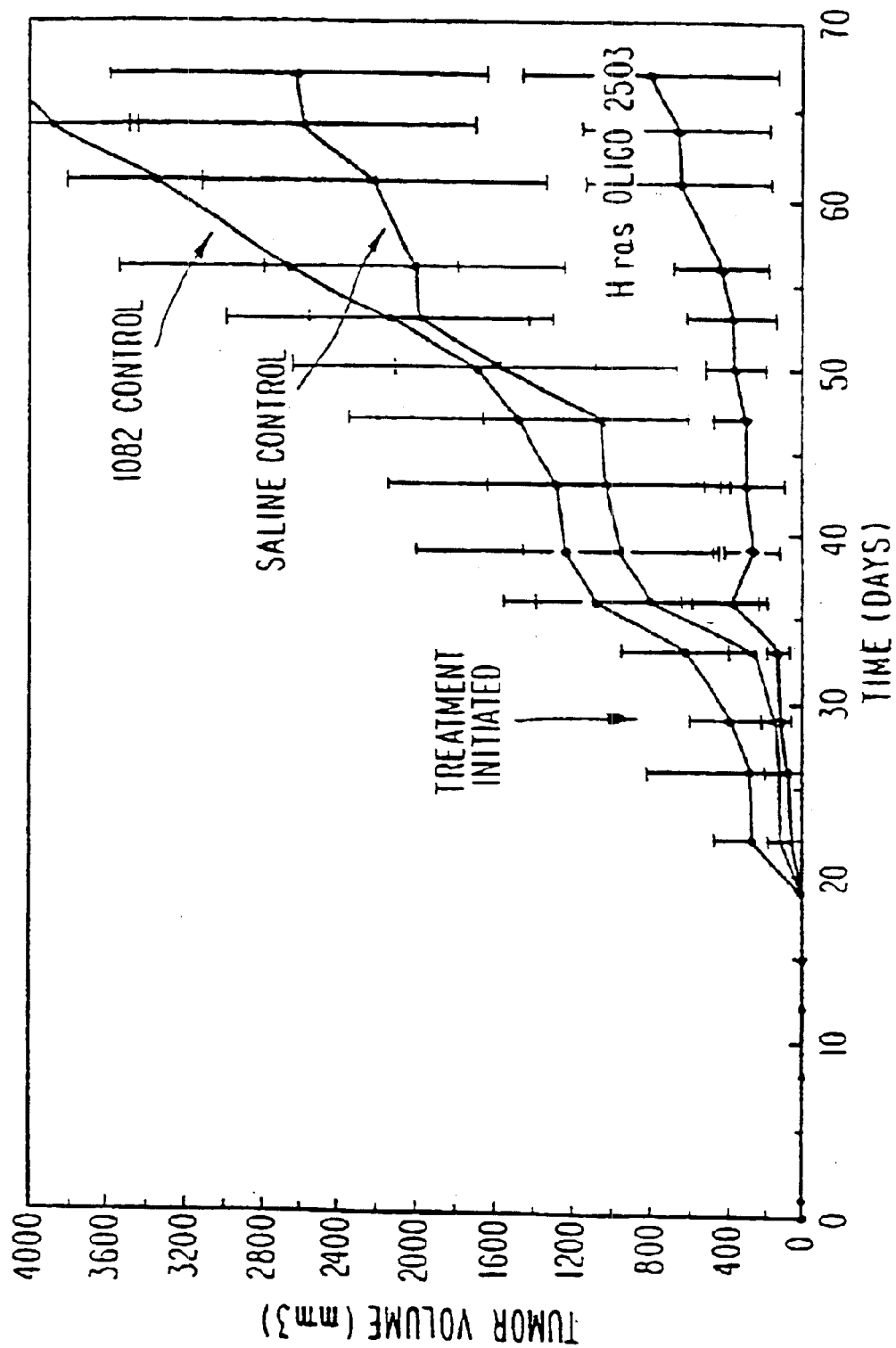
FIG. 4 is a line graph showing anti-tumor activity of ISIS 2503 against A549 human cell tumors in nude mice.

In the first study, phosphorothioate oligonucleotides in saline were administered by intraperitoneal injection at a dosage of 20 mg/kg. Drug treatment was initiated at the time tumors first became visible (28 days following tumor cell inoculation) and treatments were performed every other day. As shown in FIG. 4, no effect on tumor growth was observed after treatment with the unrelated control phosphorothioate oligonucleotide ISIS 1082 (SEQ ID NO: 55). However, significant inhibition of tumor growth was observed for the H-ras-specific oligonucleotide ISIS 2503 (SEQ ID NO: 2). The anti-tumor effects of the H-ras compound were first observed 20 days following initiation of drug treatment and continued throughout the duration of the study.

In a related study, the anti-tumor activity of ISIS 2503 against MDA-MB-231 breast carcinoma tumors was investigated as described in Example 14. These studies employed MDA-MB-231 tumors which were established by implanting cultured cells into the mammary fat pads of athymic nude mice. In these studies, phosphorothioate oligonucleotides formulated in saline, were administered daily by intraperitoneal injection at dosages of 5, 10, and 25 mg/kg/day. Drug treatment was initiated at the time tumors first became visible. Tumor volume was calculated at days 4, 11 and 17 after tumor implantation and was measured at the maximum perpendicular diameter of the tumor. At day 4 the difference in tumor volume between the vehicle treated animals and those of the high dose ISIS 2503 (25 mg/kg/day) treated animals was minimal, 25 mm$^3$ and 45 mm$^3$, respectively. However, at day 11 the vehicle treated tumors had grown to 60 mm$^3$ while the ISIS 2503 treated animals had tumor volumes of 12 mm$^3$ (both 10 and 25 mg/kg/day doses) and 25 m$^3$ (5 mg/kg/day dose). At day 17, vehicle treated animals had tumor volumes of 175 m$^3$ while those treated with ISIS 2503 had tumor volumes of 13 mm$^3$ (25 mg/kg/day dose), 20 mm$^3$: (10 mg/kg/day dose) and 110 m$^3$ (5 mg/kg/day dose).

ISIS 2503 has also exhibited broad activity in other human tumor xenograft models including activity against tumors of mutant H-ras (MiaPaCa-2, pancreatic carcinoma cells), wild-type H-ras (MDA-MB-231, breast cancer cells, disclosed herein; HT-29 colon carcinoma cells) and unknown H-ras phenotypes (Panc-1, pancreatic carcinoma cells; H-69, lung carcinoma cells).

Figure 5:
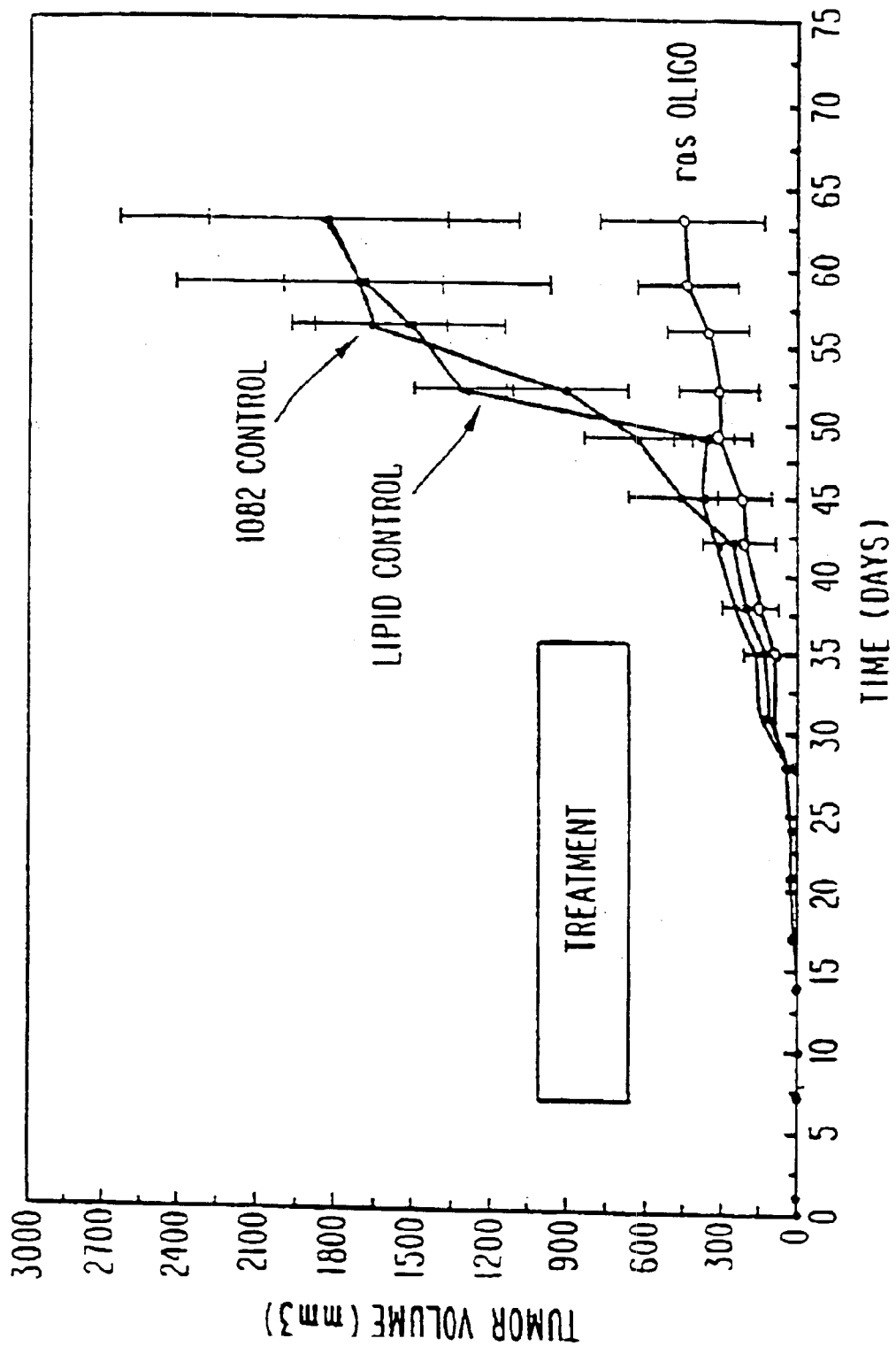
FIG. 5 is a line graph showing anti-tumor activity of ras oligo ISIS 2503, administered with cationic lipid, against A549 human cell tumors in nude mice.

In a second study, phosphorothioate oligonucleotides were prepared in a cationic lipid formulation (DMRIE:DOPE) and administered by subcutaneous injection as described in Example 15. Drug treatment was initiated one week following tumor cell inoculation and was performed three times a week for only four weeks. As was observed in the first study, administration of the H-ras-specific compound ISIS 2503 (SEQ ID NO: 2) caused a marked reduction in tumor growth whereas the unrelated control oligonucleotide (ISIS 1082) had no significant effect (FIG. 5). Reduction in tumor volume was first observed 20 days following appearance of visible tumors and continued over time throughout the remainder of the study.

Stability of 2'-modified phosphodiester oligonucleotides in cells: Modification of oligonucleotides to confer nuclease stability is required for antisense activity in cells. Certain modifications at the 2' position of the sugar have been found to confer nuclease resistance sufficient to elicit antisense effects in cells without any backbone modification. A uniformly 2'-propoxy modified phosphodiester oligonucleotide (SEQ ID NO: 3) was found to inhibit H-ras expression in T24 cells, 24 hours after administration, at a level equivalent to a phosphorothioate 2'-deoxyoligonucleotide having the same sequence. Uniform 2'-methoxy phosphodiester oligonucleotide also showed some activity. 2'-pentoxy modifications were found to be at least as active as the 2'-propoxy.

Antisense oligonucleotides active against Ki-ras:

Oligonucleotides were designed to be complementary to the 5'-untranslated region, 3'-untranslated region and coding region of the human Ki-ras oncogene. McGrath, J. P. et al. *Nature* 1983, 304, 501–506. Of the latter, oligonucleotides were targeted to codons 12 and 61 which are known sites of mutation that lead to Ki-ras-mediated transformation, and also to codon 38, which is not known to be involved in transformation. The oligonucleotides are shown in Table 8.

Ki-ras transcript, with the most active compounds being targeted to the 5'- and 3'-untranslated regions. However, significant inhibition of Ki-ras expression was also observed for compounds directed against wild type codons 12 and 61. Compounds that displayed significant activity were effective against all three carcinoma cell lines tested.

Figure 6:
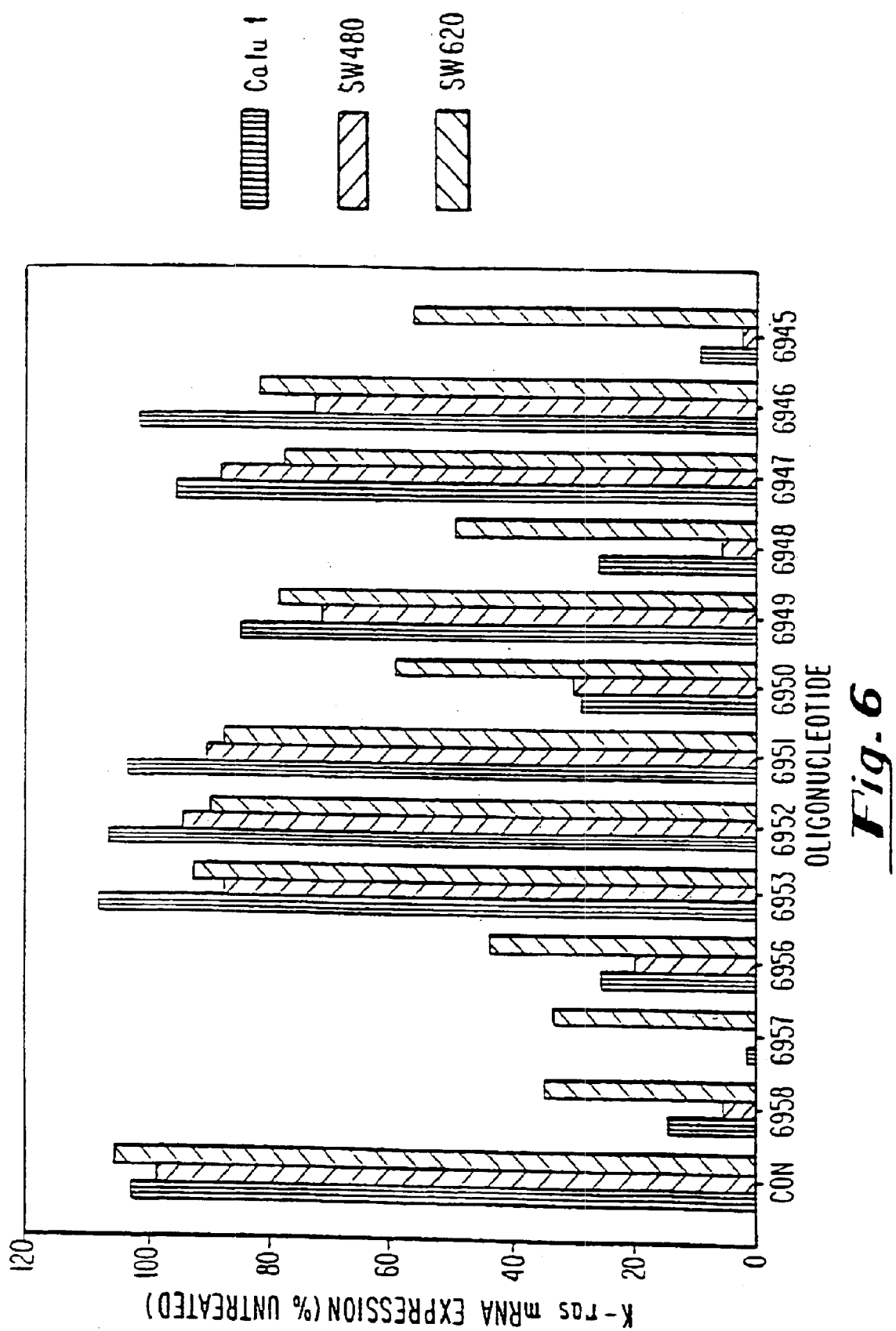
FIG. 6 is a bar graph showing antisense inhibition of Ki-ras mRNA expression in three human colon carcinoma cell lines, Calu1, SW480 and SW620.
Figure 7:
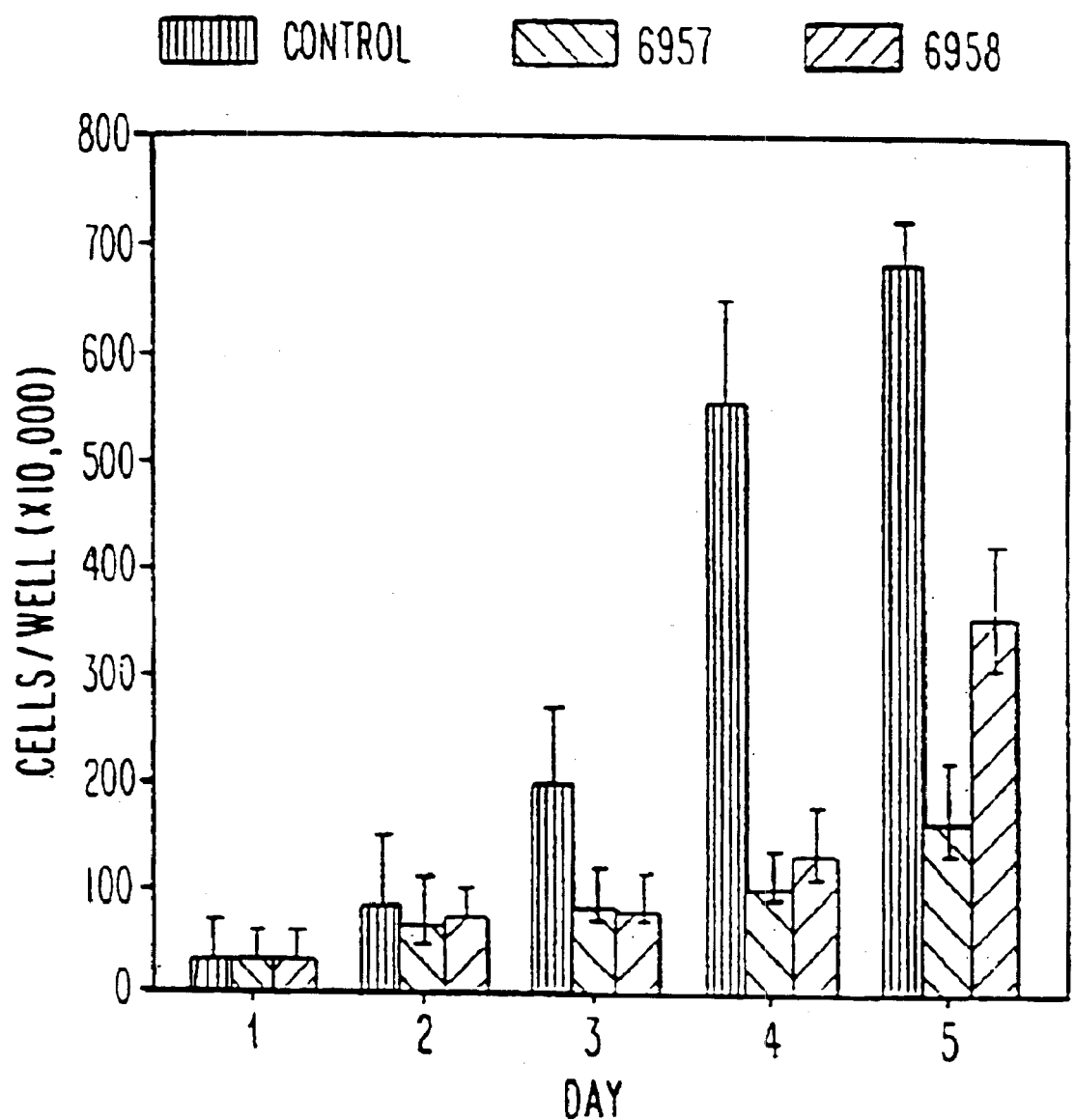
FIG. 7 is a bar graph showing inhibition of SW480 human carcinoma cell line :proliferation by Ki-ras specific oligonucleotides ISIS 6957 and ISIS 6958.

Dose response analysis of these compounds demonstrated that ISIS 6958 and ISIS 6957, both of which target the 5'-UTR, are the most potent inhibitors of Ki-ras in this series of oligonucleotides. These oligonucleotides were examined for their ability to inhibit proliferation of Ki-ras transformed cell lines. The colon carcinoma cell line SW480 was treated with a single dose of oligonucleotide (200 nM) and cell number was determined over a five-day period. As shown in FIG. 7 both Ki-ras specific: oligonucleotides were effective inhibitors of proliferation of SW480 cells, with ISIS 6957 (SEQ ID NO: 21) showing greater activity than ISIS 6958 (SEQ ID NO: 20 ). This difference in activity correlates well with the inhibition of Ki-ras mRNA expression (FIG. 6).

Selectivity of inhibition of mutant Ki-ras relative to normal Ki-ras: Oligonucleotides targeted to Ki-ras have been examined for their ability to selectively inhibit mutant Ki-ras relative to normal Ki-ras. Two cell lines were employed: the SW480 cell line that expresses mutant Ki-ras (codon 12, G to T transversion) and a cell line (HeLa) that expresses normal Ki-ras. Two oligonucleotides were tested: ISIS 6957, SEQ ID NO: 21, a 20mer phosphorothioate targeted to the 5'-untranslated region of Ki-ras, and ISIS 7453, SEQ ID NO: 32, a 15 mer phosphorothioate targeted to the Ki-ras codon 12 region. Ki-ras mRNA levels were measured 24 hours after treatment. The codon 12-directed compound was effective in the cell line expressing mutant Ki-ras (87% inhibition vs. 18% inhibition in HeLa cells). However, the Ki-ras oligonucleotide targeted to the 51-untranslated region was a potent inhibitor (95% inhibition) of Ki-ras expression in both cell lines. Selectivity for mutant Ki-ras was found to be dependent on oligonucleotide concentration and affinity for the RNA target.

Ki-ras oligonucleotides with deoxy gaps: Phosphorothioate oligonucleotides (SEQ ID NO: 21, targeted to the 5'-untranslated region of Ki-ras) were synthesized with

TABLE 8

Antisense Olionucleotides Complementary to Human Ki-ras

| ISIS # | SEQUENCE | TARGET | SEQ ID NO: |
|---|---|---|---|
| 6958 | CTG CCT CCG CCG CCG CGG CC | 5' UTR/5' cap | 20 |
| 6957 | CAG TGC CTG CGC CGC GCT CG | 5'-UTR | 21 |
| 6956 | AGG CCT CTC TCC CGC ACC TG | 5'-UTR | 22 |
| 6953 | TTC AGT CAT TTT CAG CAG GC | AUG | 23 |
| 6952 | TTA TAT TCA GTC ATT TTC AG | AUG | 24 |
| 6951 | CAA GTT TAT ATT CAG TCA TT | AUG | 25 |
| 6950 | GCC TAC GCC ACC AGC TCC AAC | Codon 12 (WT) | 26 |
| 6949 | CTA CGC CAC CAG CTC CA | Codon 12 (WT) | 27 |
| 6948 | G TAC TCC TCT TGA CCT GCT GT | Codon 61 (WT) | 28 |
| 6947 | CCT GTA GGA ATC CTC TAT TGT | Codon 38 | 29 |
| 6946 | GGT AAT GCT AAA ACA AAT GC | 3'-UTR | 30 |
| 6945 | GGA ATA CTG GCA CTT CGA GG | 3'-UTR | 31 |
| 7453 | TAC GCC AAC AGC TCC | Codon 12 (G→T mut.) | 32 |
| 7679 | TTT TCA GCA GGC CTC TCT CC | 5'-UTR/AUG | 33 |

Twelve Ki-ras-specific oligonucleotides were screened for antisense activity against three colon carcinoma cell lines that contain a mutation at codon 12 in the Ki-ras oncogene and evaluated by measurement of Ki-ras mRNA levels. As shown in FIG. 6, half of the tested compounds displayed significant activity (at least 40% inhibition) against the 2'-O-methyl modifications flanking central 2'-deoxy gap regions of 6 or 8 nucleotides in length. Both gapped oligonucleotides were active against Ki-ras expression as determined by Northern blot analysis. A uniformly 2'-O-methylated compound (no deoxy gap) was inactive. An additional oligonucleotide, ISIS 7679 (SEQ ID NO: 33, complementary to the 5'untranslated/AUG region of Ki-ras), was also found to be active when synthesized with a 6- or 8-nucleotide deoxy gap.

b 2'-Methoxyethoxy analogs of ISIS 2503 (H-ras): A series of chimeric oligonucleotides were synthesized with the ISIS 2503 sequence (SEQ ID NO: 2) and various arrangements of 2'-methoxyethoxy (2'-MOE) modifications. These are shown in Table 9. All backbone linkages are phosphorothioates.

TABLE 9

2'-MOE analogs of ISIS 2503
Positions with 2'-MOE are shown in bold

| ISIS # | Sequence (5'--3 =) | SEQ ID NO: |
|---|---|---|
| 13905 | TCCGTCATCGCTCCTCAGGG | 2 |
| 13907 | TCCGTCATCGCTCCTCAGGG | 2 |
| 13909 | TCCGTCATCGCTCCTCAGGG | 2 |
| 13911 | TCCGTCATCGCTCCTCAGGG | 2 |
| 13917 | TCCGTCATCGCTCCTCAGGG | 2 |
| 13919 | TCCGTCATCGCTCCTCAGGG | 2 |
| 13920 | TCCGTCATCGCTCCTCAGGG | 2 |
| 13923 | TCCGTCATCGCTCCTCAGGG | 2 |
| 13926 | TCCGTCATCGCTCCTCAGGG | 2 |
| 13927 | TCCGTCATCGCTCCTCAGGG | 2 |

Figure 8:
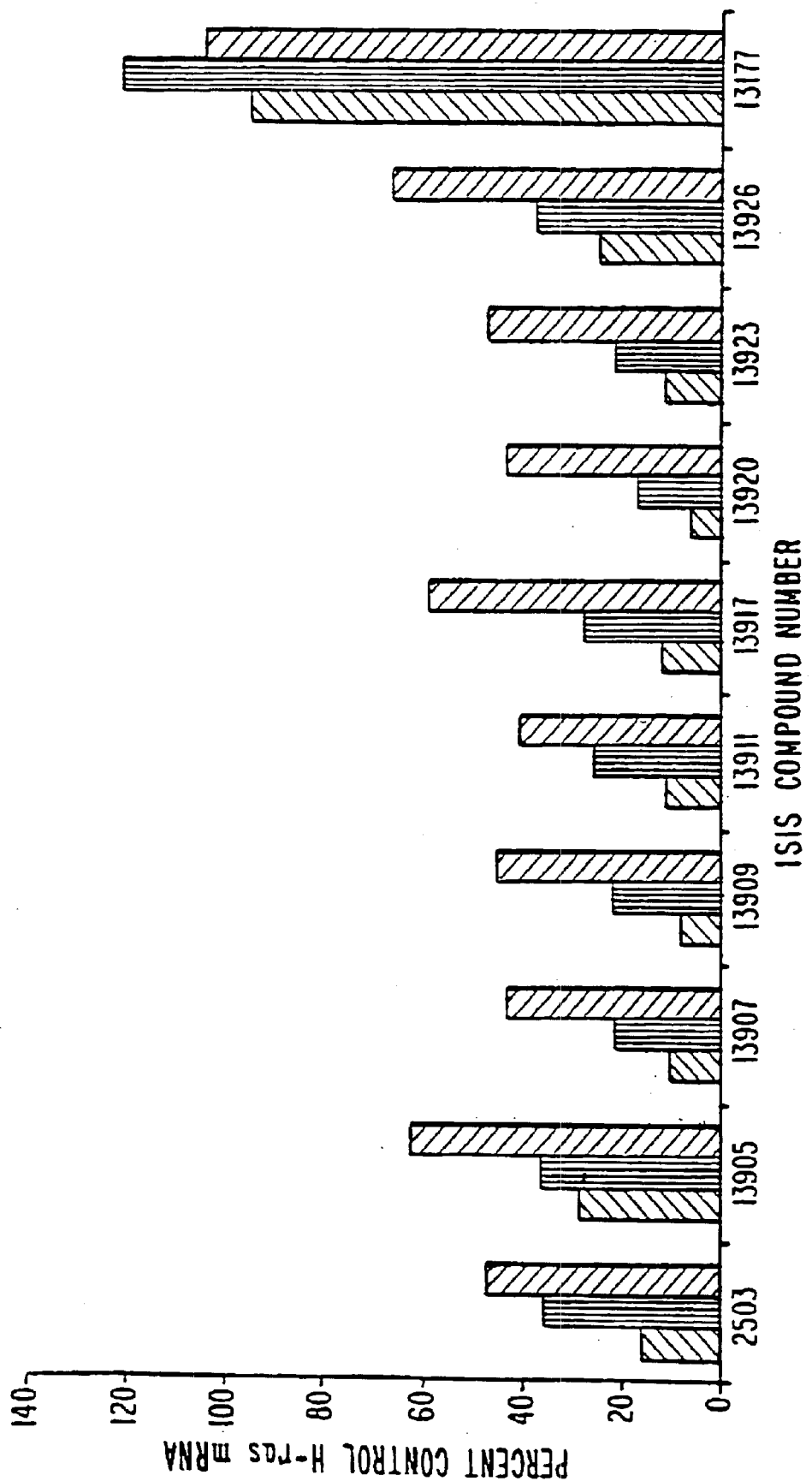
FIG. 8 is a bar graph showing reduction of H-ras mRNA levels by 2'-MOE analogs of ISIS 2503 (SEQ ID NO: 2). Black bars: 150 nM oligonucleotide dose; Diagonal hatched bars: 50 nM dose; horizontal hatched bars: 15 nM dose.

These oligonucleotides (except for 13919 and 13927 which have not yet been tested) were tested for the ability to reduce H-ras mRNA levels in T24 cells as described in Example 10 except that oligonucleotide and lipofectin were mixed in OptiMEM and kept at a constant ratio of 2.5 ug/ml lipofectin per 100 nM oligonucleotide. All of the tested compounds had activity comparable to ISIS 2503, the parent compound, with IC50's of 50 nM or below. For this reason oligonucleotides containing one or more 2'-MOE modifications are preferred for reducing ras expression. Dose responses for these compounds are shown in FIG. 8. ISIS 13177 (TCAGTAATAGCCCCACATGG; SEQ ID NO: 34) is a phosphorothioate oligodeoxynucleotide scrambled control for SEQ ID NO: 2.

MMI analogs of ISIS 2503 (H-ras): A series of chimeric oligonucleotides were synthesized with the ISIS 2503 sequence (SEQ ID NO: 2) and various placements of methylene(methylimino)backbone linkages. These are shown in Table 10. For ease of synthesis, dimers incorporating an MMI linkage were used in making these oligonucleotides. Dimers containing MMI backbone linkages are indicated by bold lettering. "$_o$" indicates a phosphodiester linkage between MMI dimers. "$_s$" indicates a phosphorothioate linkage between MMI dimers. All unmarked linkages are phosphorothioates.

TABLE 10

MMI analogs of ISIS 2503

| ISIS # | Sequence (5'--3 =) | SEQ ID NO: |
|---|---|---|
| 14896 | TCCGTCATCGCTCCTCAGGG | 2 |
| 14897 | TC$_o$CGTCATCGCTCCTCAG$_o$GG | 2 |
| 14898 | TC$_s$CGTCATCGCTCCTCAG$_s$GG | 2 |
| 14899 | TC$_o$CG$_o$TCATCGCTCCTC$_o$A$_o$GGG | 2 |
| 14900 | TC$_s$CG$_s$TCATCGCTCCTC$_s$AG$_s$AG | 2 |

Figure 9:
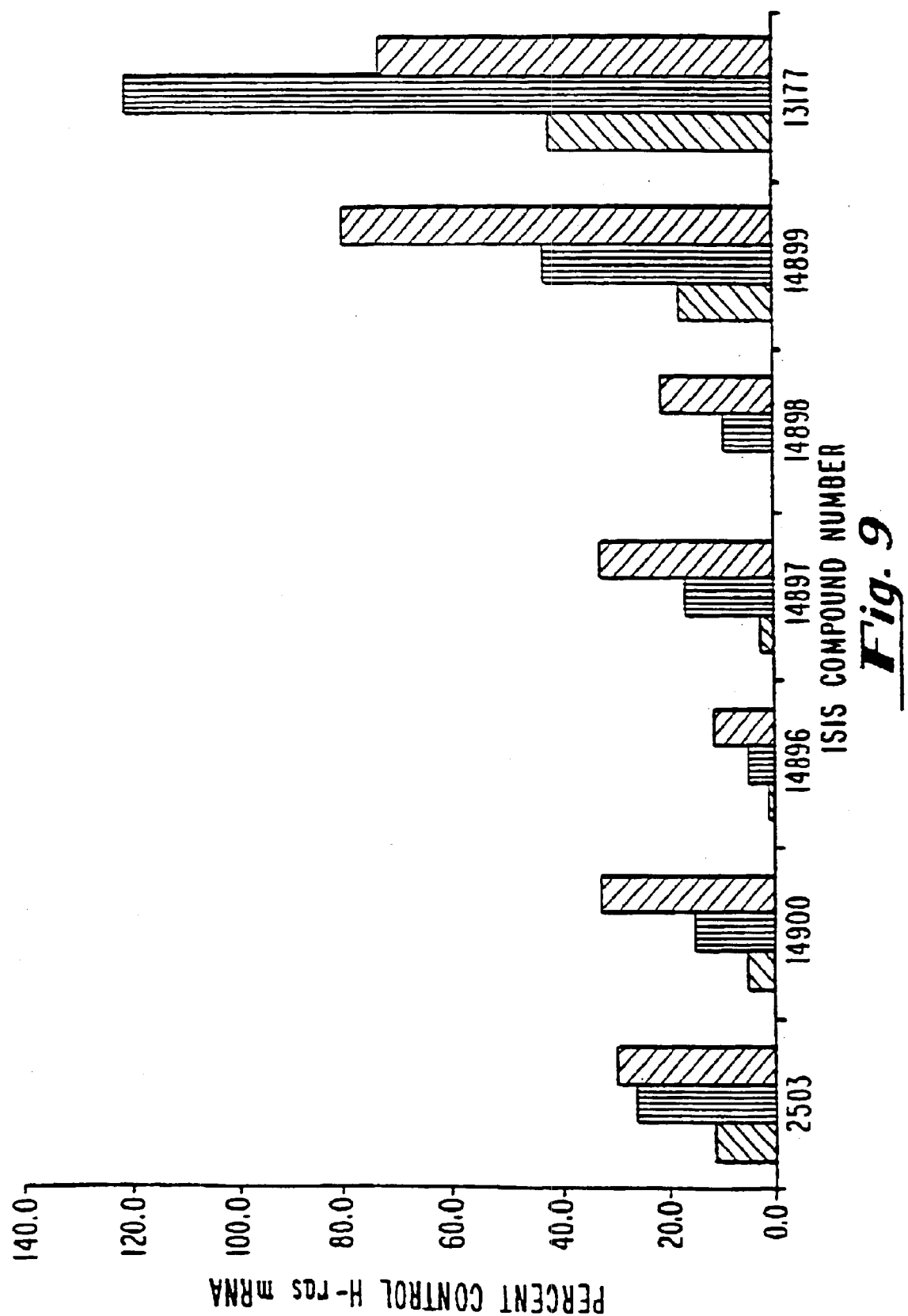
FIG. 9 is a bar graph showing reduction of H-ras mRNA levels by MMI analogs of ISIS 2503 (SEQ ID NO: 2). Black bars: 500 nM oligonucleotide dose;. Diagonal hatched bars: 100 nM dose; horizontal hatched bars: 50 nM dose.

These compounds were tested for their ability to reduce H-ras mRNA levels in T24 cells as described in Example 10 except that oligonucleotide and lipofectin were mixed in OptiMEM and kept at a constant ratio of 2.5 μg/ml lipofectin per 100 nM oligonucleotide. As shown in FIG. 9, all of these compounds were able to reduce mRNA levels by 80% or more at doses of 500 nM and below. ISIS 13177 (SEQ ID NO: 34) is a phosphorothioate oligodeoxynucleotide scrambled control for SEQ ID NO: 2. With the exception of ISIS 14899, all the MMI compounds were more active than the parent deoxyphosphorothioate compound, ISIS 2503. Several compounds (ISIS 14896, 14897, 14898) achieved nearly complete ablation of ras mRNA. Oligonucleotides containing one or more MMI modifications are therefore highly preferred for reducing ras expression.

Antisense oligonucleotides active against N-ras:

A series of phosphorothioate oligodeoxynucleotides were designed to target human N-ras using the published sequence (Genbank accession number HSNRASR, x02751). These compounds were tested for their ability to reduce N-ras levels in T24 cells as described in Example 10 except that the probe was an N-ras cDNA probe (purchased from Oncogene Science, Cambridge Mass.; catalog no. HP129) and oligonucleotide and lipofectin were mixed in OptiMEM and kept at a constant ratio of 2.5 ug/ml lipofectin per 100 nM oligonucleotide.

Figure 10:
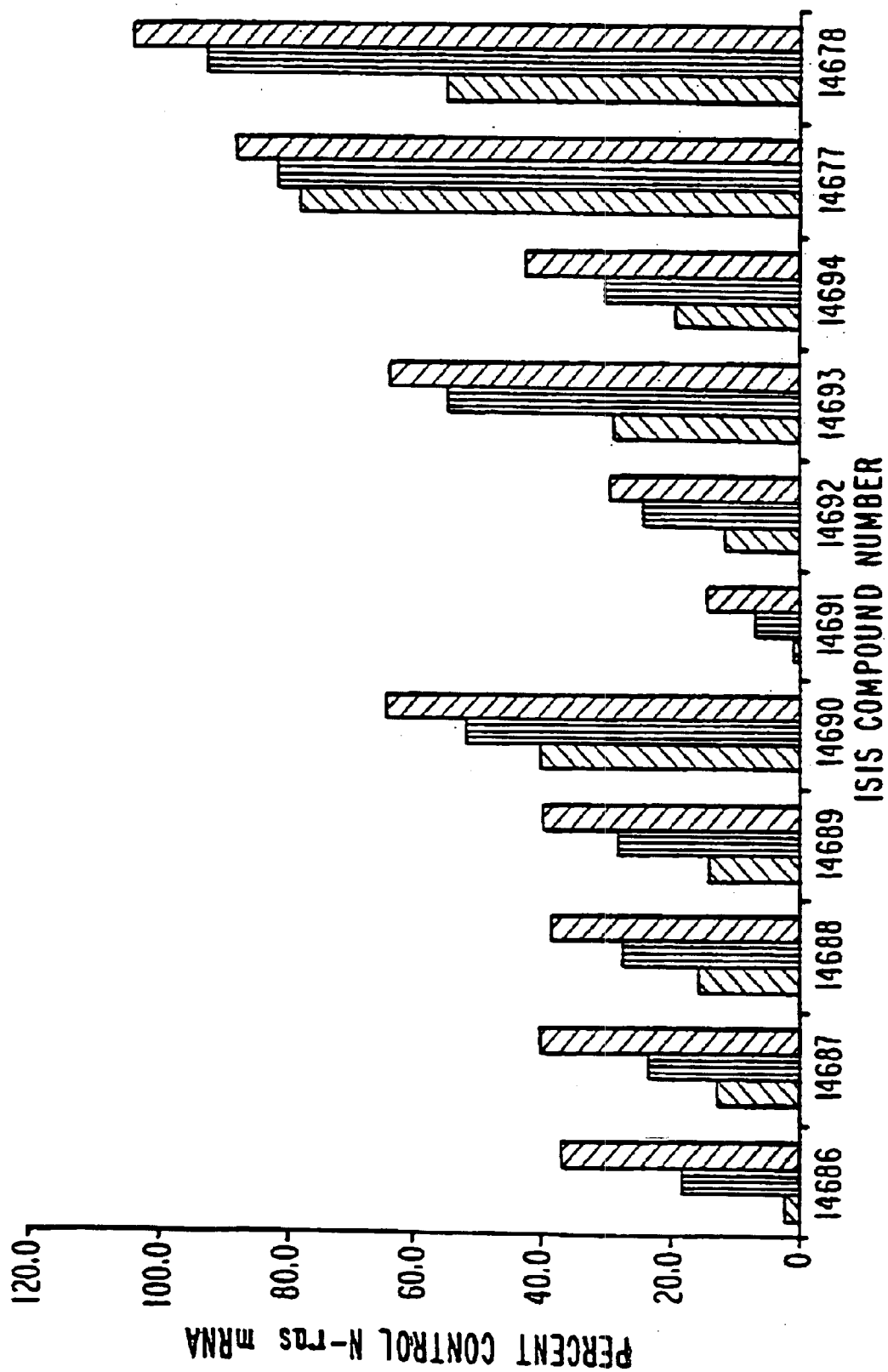
FIG. 10 is a bar graph showing reduction of N-ras mRNA levels by oligonucleotides 14686–14694, 14677 and 14678. Black bars: 400 nM oligonucleotide dose; Diagonal hatched bars:, 200 nM dose; horizontal hatched bars: 100 nM dose.

These oligonucleotides, and the percent reduction in N-ras mRNA demonstrated for each, are shown in Table 11. Oligonucleotides shown in bold (SEQ ID NO: 44, 45, 46, 47, 49 and 52) demonstrated greater than 30% reduction of ras mRNA when screened at a 300 nM dose and are considered active in this assay. These sequences are therefore preferred. Of these oligonucleotides 14686, 14687, 14688, 14691 and 14694 (SEQ ID NO: 44, 45, 46, 49 and 52) showed greater than 50% inhibition. Dose response curves were obtained for oligonucleotides 14677, 14678, 14686, 14687, 14688, 14689, 14690, 14891, 14692, 14693, and 14694. These are shown in FIG. 10. As can be seen from the figure, ISIS 14686 and ISIS 14691 (SEQ ID NO: 44 and 49, respectively) gave nearly complete ablation of N-ras mRNA at a 400 nM dose.

TABLE 11

Oligonucleotides targeted to human N-ras

| ISIS # | Sequence (5'--3 =) | Target Region | % Reduced | SEQ ID NO: |
|---|---|---|---|---|
| 14677 | CCGGGTCCTAGAAGCTGCAG | 5' UTR | 0.0 | 35 |
| 14678 | TAAATCAGTAAAAGAAACCG | 5' UTR | 0.0 | 36 |
| 14679 | GGACACAGTAACCAGGCGGC | 5' UTR | 0.0 | 37 |
| 14680 | AACAGAAGCTACACCAAGGG | 5' UTR | 0.0 | 38 |
| 14681 | CAGACCCATCCATTCCCGTG | 5' UTR | 0.0 | 39 |
| 14682 | GCCAAGAAATCAGACCCATC | 5' UTR | 0.0 | 40 |
| 14683 | AGGGGGAAGATAAAACCGCC | 5' UTR | 0.0 | 41 |
| 14684 | CGCTTCCATTCTTTCGCCAT | 5' UTR | 0.0 | 42 |
| 14685 | CCGCACCCAGACCCGCCCCT | 5' UTR | 0.0 | 43 |
| 14686 | CAGCCCCCACCAAGGAGCGG | 5' UTR | 61.0 | 44 |
| 14687 | GTCATTTCACACCAGCAAGA | AUG | 50.2 | 45 |
| 14688 | CAGTCATTTCACACCAGCAA | AUG | 60.5 | 46 |
| 14689 | CTCAGTCATTTCACACCAGC | AUG | 38.4 | 47 |
| 14690 | CGTGGGCTTGTTTTGTATCA | Coding | 0.2 | 48 |
| 14691 | CCATACAACCCTGAGTCCCA | 3' UTR | 58.3 | 49 |
| 14692 | CAGACAGCCAAGTGAGGAGG | 3' UTR | 0.0 | 50 |
| 14693 | CCAGGGCAGAAAAATAACAG | 3' UTR | 0.0 | 51 |
| 14694 | TTTGTGCTGTGGAAGAACCC | 3' UTR | 50.7 | 52 |
| 14695 | GCTATTAAATAACAATGCAC | 3' UTR | 0.0 | 53 |
| 14696 | ACTGATCACAGCTATTAAAT | 3' UTR | 0.0 | 54 |

The following examples illustrate the present invention and are not intended to limit the same.

EXAMPLES

Example 1

Synthesis and Characterization of Oligonucleotides

Unmodified oligodeoxynucleotides are synthesized on an automated DNA synthesizer (Applied Biosystems model 380B) using standard phosphoramidite chemistry with oxidation by iodine. â-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy â-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.* 1993, 36, 831–841. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-â-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-31-phosphoramidite intermediates.

The synthesis of 2'-deoxy--2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy--2'-fluorouridine was accomplished by the modification of a known procedure in which 2, 2'anhydro-1-β-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, P., *Helv. Chim. Acta* 1995, 78,486–504. For ease of synthesis, the last nucleotide was a deoxynucleotide. 2'-O—$CH_2CH_2OCH_3$.cytosines may be 5-methyl cytosines.

Synthesis of 5-Methyl cytosine monomers:

2,2'-Anhydro[1-(â-D-arabinofuranosyl)-5-methyluridine]:

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 ML) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyl-uridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product).

The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methyl-cytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated NaHCO, (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL)), and the extracts were combined, dried over $MgSO_4$ and concentrated. The residue obtained was chromatographed on a 1.5 kg silica column using EtOAcHexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al. *Nucl. Acids Res.* 1993, 21, 3197–3203) using commercially available phosphoramidites (Glen Research, Sterling Va. or ChemGenes, Needham Mass.).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. *Acc. Chem. Res.* 1995, 28, 366–374. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. *Science* 1991, 254, 1497).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. *J. Biol. Chem.* 1991, 266:18162–18171. Results obtained with HPLC-purified material were similar to those obtained with non-HPLC purified material.

Example 2 ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. The plasmids pT24-C3, containing the c-H-ras1 activated oncogene (codon 12, GGC→GTC), and pbc-N1, containing the c-H-ras proto-oncogene, were obtained from the American Type Culture Collection (Bethesda, Md.). The plasmid pT3/T7 luc, containing the 1.9 kb firefly luciferase gene, was obtained from Clontech Laboratories (Palo Alto, Calif.). The oligonucleotide PCR primers were used in standard PCR reactions using mutant and non-mutant H-ras genes as templates. These primers produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were used in standard PCR reactions using a commercially available plasmid (pT3/T7-Luc) (Clontech), containing the luciferase reporter gene, as a template. These primers yield a product of approximately 1.9 kb corresponding to the luciferase gene, flanked by unique HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter. These plasmid constructions contain sequences encoding amino acids 1–22 of activated (RA2) or normal (RA4) H-ras proteins fused in frame with sequences coding for firefly luciferase. Translation initiation of the ras-luciferase fusion mRNA is dependent upon the natural H-ras AUG codon. Both mutant and normal H-ras luciferase fusion constructions were confirmed by DNA sequence analysis using standard procedures.

Example 3

Transfection of Cells with Plasmid DNA

Transfections were performed as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY, with the following modifications. HeLa cells were plated on 60 mm dishes at $5 \times 10^5$ cells/dish. A total of 10 µg or 12 µg of DNA was added to each dish, of which 1 µg was a vector expressing the rat glucocorticoid receptor under control of the constitutive Rous sarcoma virus (RSV) promoter and the remainder was ras-luciferase reporter plasmid. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pretreated with antisense oligonucleotides prior to activation of reporter gene expression by dexamethasone.

Example 4

Oligonucleotide Treatment of Cells

Following plasmid transfection, cells were washed with phosphate buffered saline prewarmed to 37° C. and Opti-MEM containing 5 µg/mL N-[1-(2,3-dioleyloxy)propyl]-N, N,N, -trimethylammonium chloride (DOTMA) was added to each plate (1.0 ml per well). Oligonucleotides were added from 50 µM stocks to each plate and incubated for 4 hours at 37° C. Medium was removed and replaced with DMEM containing 10% fetal bovine serum and the appropriate oligonucleotide at the indicated concentrations and cells were incubated for an additional 2 hours at 37° C. before reporter gene expression was activated by treatment of cells with dexamethasone to a final concentration of 0.2 µM. Cells were harvested and assayed for luciferase activity fifteen hours following dexamethasone stimulation.

Example 5

Luciferase Assays

Luciferase was extracted from cells by lysis with the detergent Triton X-100 as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. A Dynatech ML1000 luminometer was used to measure peak luminescence upon addition of luciferin (Sigma) to 625 µM. For each extract, luciferase assays were performed multiple times, using differing amounts of extract to ensure that the data were gathered in the linear range of the assay.

Example 6

Melting Curves

Absorbance vs temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 µM each strand determined from the absorbance at 85° C. and extinction coefficients calculated according to Puglisi and Tinoco, *Methods in Enzymol.* 1989, 180, 304–325. $T_m$ values, free energies of duplex formation and association constants were obtained from fits of data to a two state model with linear sloping baselines. Petersheim, M. and Turner, D. H., *Biochemistry* 1983, 22, 256–263. Reported parameters are averages of at least three experiments. For some oligonucleotides, free energies of duplex formation were also obtained from plots of $T_m^{-1}$ vs $\log_{10}$ (concentration). Borer, P. N., Dengler, B., Tinoco, I., Jr., and Uhlenbeck, O. C., *J. Mol. Biol.*, 1974, 86, 843–853.

Example 7

Gel Shift Assay

The structured ras target transcript, a 47-nucleotide hairpin containing the mutated codon 12, was prepared and mapped as described in Lima et al., *Biochemistry* 1991, 31, 12055–12061. Hybridization reactions were prepared in 20 µl containing 100 mM sodium, 10 mM phosphate, 0.1 mM EDTA, 100 CPM of T7-generated RNA (approximately 10 pM), and antisense oligonucleotide ranging in concentration from 1 pM to 10 µM. Reactions were incubated 24 hours at 37° C. Following hybridization, loading buffer was added to the reactions and reaction products were resolved on 20% native polyacrylamide gels, prepared using 45 mM tris-borate and 1 mM MgCl$_2$ (TBM). Electrophoresis was carried out at 10° C. and gels were quantitated using a Molecular Dynamics Phosphorimager.

Example 8

RNase H Analysis

RNase H assays were performed using a chemically synthesized 25-base oligoribonucleotide corresponding to bases +23 to +47 of activated (codon 12, G→U) H-ras mRNA. The 5' end-labeled RNA was used at a concentration of 20 nM and incubated with a 10-fold molar excess of antisense oligonucleotide in a reaction containing 20 mM Tris-Cl, pH 7.5, 100 mM KCl, 10 mM $MgCl_2$, 1 mM dithiothreitol, 10 µg tRNA and 4 U RNasin in a final volume of 10 µl. The reaction components were preannealed at 37° C. for 15 minutes then allowed to cool slowly to room temperature. HeLa cell nuclear extracts were used as a source of mammalian RNase H. Reactions were initiated by addition of 2 µg of nuclear extract (5 µl) and reactions were allowed to proceed for 10 minutes at 37° C. Reactions were stopped by phenol/chloroform extraction and RNA components were precipitated with ethanol. Equal CPMs were loaded on a 20% polyacrylamide gel containing 7M urea and RNA cleavage products were resolved and visualized by electrophoresis followed by autoradiography. Quantitation of cleavage products was performed using a Molecular Dynamics Densitometer.

Example 9 ras Transactivation Reporter Gene System

The expression plasmid pSV2-oli, containing an activated (codon 12, GGC→GTC) H-ras cDNA insert under control of the constitutive SV40 promoter, was a gift from Dr. Bruno Tocque (Rhone-Poulenc Sante, vitry, France). This plasmid was used as a template to construct, by PCR, a H-ras expression plasmid under regulation of the steroid-inducible mouse mammary tumor virus (MMTV) promoter. To obtain H-ras coding sequences, the 570 bp coding region of the H-ras gene was amplified by PCR. The PCR primers were designed with unique restriction endonuclease sites in their 5'-regions to facilitate cloning. The PCR product containing the coding region of the H-ras codon 12 mutant oncogene was gel purified, digested, and gel purified once again prior to cloning. This construction was completed by cloning the insert into the expression plasmid pMAMneo (Clontech Laboratories, Calif.).

The ras-responsive reporter gene pRDO53 was used to detect ras expression. Owen et al., *Proc. Natl. Acad. Sci. U.S.A.* 1990, 87, 3866–3870.

Example 10

Northern Blot Analysis of ras Expression in Vivo

The human urinary bladder cancer cell line T24 was obtained from the American Type Culture Collection (Rockville Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 µl DOTMA was added. Oligonucleotide was then added to the desired concentration. After 4 hours of treatment, the medium was replaced with McCoy's medium. Cells were harvested 48 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY.

The human epithelloid carcinoma cell line HeLa 229 was obtained from the American Type Culture Collection (Bethesda, Md.). HeLa cells were maintained as monolayers on 6-well plates in Dulbecco's Modified Eagle's medium (DMEM) supplemented with 10% fetal bovine serum and 100 U/ml penicillin. Treatment with oligonucleotide and isolation of RNA were essentially as described above for T24 cells.

Northern hybridization: 10 µg of each RNA was electrophoresed on a 1.2% agarose/formaldehyde gel and transferred overnight to GeneBind 45 nylon membrane (Pharmacia LKB, Piscataway, N.J.) using standard methods. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. RNA was UV-crosslinked to the membrane. Double-stranded $^{32}$P-labeled probes were synthesized using the Prime a Gene labeling kit (Promega, Madison Wis.). The ras probe was a SalI-NheI fragment of a cDNA clone of the activated (mutant) H-ras mRNA having a GGC-to-GTC mutation at codon-12. The control probe was G3PDH. Blots were prehybridized for 15 minutes at 68° C. with the QuickHyb hybridization solution (Stratagene, La Jolla, Calif.). The heat-denatured radioactive probe ($2.5 \times 10^6$ counts/2 ml hybridization solution) mixed with 100 µl of 10 mg/ml salmon sperm DNA was added and the membrane was hybridized for 1 hour at 68° C. The blots were washed twice for 15 minutes at room temperature in 2×SSC/0.1% SDS and once for 30 minutes at 60° C. with 0.1×SSC/0.1% SDS. Blots were autoradiographed and the intensity of signal was quantitated using an ImageQuant PhosphorImager (Molecular Dynamics, Sunnyvale, Calif.). Northern blots were first hybridized with the ras probe, then stripped by boiling for 15 minutes in 0.1×SSC/0.1% SDS and rehybridized with the control G3PDH probe to check for correct sample loading.

Example 11

Antisense Oligonucleotide Inhibition of Proliferation of Cancer Cells

Cells were cultured and treated with oligonucleotide essentially as described in Example 10. Cells were seeded on 60 mm plates and were treated with oligonucleotide in the presence of DOTMA when they reached 70% confluency.

Time course experiment: On day 1, cells were treated with a single dose of oligonucleotide at a final concentration of 100 nM. The growth medium was changed once on day 3 and cells were counted every day for 5 days, using a counting chamber. Dose-response experiment: Various concentrations of oligonucleotide (10, 25, 50, 100 or 250 nM) were added to the cells and cells were harvested and counted 3 days later. Oligonucleotides 2570, 3985 and 4690 were tested for effects on T24 cancer cell proliferation.

Example 12

Synthesis of 2-(amino)adenine-substituted Oligonucleotides

Oligonucleotides are synthesized as in Example 1, with the following exception: at positions at which a 2-(amino) adenine is desired, the standard phosphoramidite is replaced with a commercially available 2-aminodeoxyadenosine phosphoramidite (Chemgenes).

Example 13

Culture of A549 Cells

A549 cells (obtained from the American Type Culture Collection, Bethesda Md.) were grown to confluence in

Example 14

Oligonucleotide Treatment of Human Tumor Cells in Nude Mice—Intraperitoneal Injection Human lung carcinoma A549 cells were harvested and $5 \times 10^6$ cells (200 µl) were injected subcutaneously into the inner thigh of nude mice. Palpable tumors develop in approximately one month. Phosphorothioate oligonucleotides ISIS 2503 and 1082 (unrelated control) were administered to mice intraperitoneally at a dosage of 20 mg/kg body weight, every other day for approximately ten weeks. Mice were monitored for tumor growth during this time.

Human breast carcinoma MDA-MB-231 cells were harvested and $5 \times 10^6$ cells (200 µl) were injected subcutaneously into the mammary fat pads of athymic nude mice. Palpable tumors develop in approximately one month. Phosphorothioate oligonucleotides ISIS 2503 and a vehicle containing no oligonucleotide were administered to mice intraperitoneally at a dosages of 5, 10, and 25 mg/kg/day body weight, every day for approximately 20 days. Mice were monitored for tumor growth during this time.

Example 15

Oligonucleotide Treatment of Human Tumor Cells in Nude Mice—Subcutaneous Injection with Cationic Lipid Human lung carcinoma A549 cells were harvested and $5 \times 10^6$ cells (200 µl) were injected subcutaneously into the inner thigh of nude mice. Palpable tumors develop in approximately one month. Phosphorothioate oligonucleotides ISIS 2503 and the unrelated control oligonucleotide 1082 (dosage 5 mg/kg), prepared in a cationic lipid formulation (DMRIE/DOPE, 60 mg/kg) were administered to mice subcutaneously at the tumor site. Drug treatment began one week following tumor cell inoculation and was given twice a week for only four weeks. Mice were monitored for tumor growth for a total of nine weeks.

Example 16

Stability of 2' Modified Oligonucleotides in T24 Cells

T24 bladder cancer cells were grown as described in Example 10. Cells were treated with a single dose (1 µM) of oligonucleotide and assayed for H-ras mRNA expression by Northern blot analysis 24 hours later. Oligonucleotides tested were analogs of ISIS 2570 (SEQ ID NO: 3), a 17 mer targeted to H-ras codon 12.

Example 17

Activity of Ki-ras Oligonucleotides Against Three Colon Carcinoma Cell Lines Human colon carcinoma cell lines Calu 1, SW480 and SW620 were obtained from the American Type Culture Collection (ATCC) and cultured and maintained as described for HeLa cells in Example 10. Cells were treated with a single dose of oligonucleotide (200 mM) and Ki-ras mRNA expression was measured by Northern blot analysis 24 hours later. For proliferation studies, cells were treated with a single dose of oligonucleotide (200 nM) at day zero and cell number was monitored over a five-day period.

Example 18

Oligonucleotide Inhibition of Mutant vs. Wild-type Ki-ras

SW480 cells were cultured as in the previous example. HeLa cells were cultured as in Example 10. Cells were treated with a single dose (100 nM) of oligonucleotide and mRNA levels were determined by Northern blot analysis 24 hours later.

Example 19

Effects of Antisense Inhibition of H-ras on Patients with Advanced Cancer-24 Hour Weekly Infusion Nineteen fully evaluable patients with a range of cancer types including colorectal (9) sarcoma (4) and other (6; one each breast, NSCLC (non-small cell lung carcinoma), renal, melanoma, bladder and unknown) received ISIS 2503 by a 24 hour weekly infusion for up to nine doses of 3, 6, 12, 18 and 24 mg/kg/wk for three weeks. A single dose escalation to the next dose level was permitted for stable or responding patients. There were ten men and nine women with a median age of 61 (range 44–69) and a median ECOG Performance Status (PS) of 1 (range 0–2). ISIS 2503 infusion was well tolerated. Eligibility required an ECOG PS of $\leq 2$ and histologically confirmed cancer with measurable or evaluable disease and no effective therapy. Normal organ function was also required (creatinine$\leq 1.5$ mg/dL; bilirubin$\leq 1.5$ mg/dL; AST/ALT<2.5× Upper limit of normal detection (ULN); ANC>1500 cells/il; platelet count>100,000/uL; hemoglobin>9 g/dL and prothrombin time/activated partial thromboplastin (PT/aPTT) $\leq$ULN). Patients also had no underlying disease state associated with active bleeding nor were they on any anti-coagulation therapy or had any history of brain or CNS metastases. All patients were treated for three cycles (9 weeks) at doses of 3 (1 patient), 6 (3 patients; 1 patient escalated to the 12 mg/kg dose), 12 (3 patients), 18 (6 patients) and 24 (7 patients) mg/kg/wk prior to response assessment.

Clinical Responses in Patients with Advanced Cancer-24 Hour Weekly Infusion Pharmacokinetic studies demonstrated a dose-related increase in plasma concentrations with steady-state concentrations of 2.03,' 3.95, 8.84 and 14.83 µg/ml for the 4 doses studied. Approximately 65% of the drug is intact at 24 hours at all doses. Serological evidence of complement activation was observed at the end of the infusion, but no clinical evidence of complement activation was apparent. Dose limiting toxicity was observed at a 24/mg/kg/wk dose level and consisted of one patient with acute renal failure and one with transient renal insufficiency and grade 3 hyperbilirubinemia. The dose limiting toxicity only occurred, however, at the first dose of ISIS 2503 and no recurrent or cumulative toxicity was seen. Three patients developed a syndrome associated with their first infusion characterized by an increase creatinine and anemia with evidence of microangiopathy in 2 of the 3 cases. In two of the cases, the toxicity was self-limiting and rapidly resolved in 3–7 days. The third episode proceeded to acute renal failure and the patient expired from progressive cancer on dialysis. Dose escalation was stopped at the 24 mg/kg/wk dose level due to two such events. Eighteen mg/kg/wk was determined to be the maximal tolerable dose. At doses>6 mg/kg, grade 1–2 post-infusion fevers were seen. These were managed with acetaminophen and/or NSAIDS. One patient with a grade 2 allergic rash at the 18. mg/kg dose level and this patient was not re-challenged. Transient grade 1 thrombocytopenia was seen in several patients treated at the higher doses. One patient developed a grade 3 thrombocytopenia coincident with her rapidly reversible renal insufficiency. No objective responses have been seen, though one patient with melanoma had stable disease at 9 weeks and continued on therapy. She experienced a minor response with shrinkage of liver metastases. She continued on the therapy with stable disease/minor response for 9 cycles (27 weeks) until developing brain metastases. Nine patients experienced progression of disease. The remaining patients were not evaluable for response due to early withdrawal. In conclusion,. ISIS 2503 can be safely administered via a weekly 24 hour continuous intravenous infusion at doses of ≦18 mg/kg/wk.

Example 20

Effects of Antisense Inhibition of H-ras on Patients with Advanced Cancer-14 Day Continuous Infusion (ISIS 2503-CS1)

A continuous intravenous infusion of ISIS 2503 was administered to 23 evaluable patients (9 male, 14 female; age range 39–74 years) at doses of 1.0 (3 patients), 2.0 (3 patients), 3.0 (3 patients), 4.5 (3 patients), 6.0 (3 patients), 8.0 (3 patients) and 10.0 (4 patients) mg/kg/d by 14-day continuous infusion, repeated every 21 days. A single patient was studied at lower doses and shorter treatment durations to guard against early toxicity related to suppression of H-ras expression. This patient received 0.5–1.0 mg/kg/d of ISIS 2503. Subsequently, patients received 69 cycles of ISIS 2503 and no dose-limiting toxicities were observed. Eligibility required an ECOG PS of ≦2 and histologically confirmed cancer with measurable or evaluable solid tumor or lymphoma and no effective therapy. Normal organ function was also required (creatinine≦1.5 mg/dL; bilirubin≦2.0 mg/dL; AST/ALT<2.5× ULN (≦5× in the presence of hepatic metastasis); ANC>1500/m$^3$; platelet count>100,000/m$^3$; hemoglobin>9 g/dL and prothrombin time/activated partial thromboplastin (PT/aPTT) normal). Patients also had no underlying disease state associated with active bleeding nor were they on any anti-coagulation therapy or had any uncontrolled CNS involvement by tumor. Pregnant women were also excluded. Endpoints involved the measure of toxicity National Cancer Institute-Common Toxicity Criteria (NCI-CTC), tumor response, pharmacokinetics and H-ras mRNA expression in peripheral blood mononuclear cells.

ISIS 2503 was supplied as a sterile solution in 1 ml or 10 ml vials containing phosphate buffered saline (pH 7.4) at a concentration of 10 mg/ml. Prior to administration ISIS 2503 was diluted in normal saline for infusion by a volumetric infusion pump with a 0.22 μm in-line filter.

Patient characteristics included three patients with colon, renal and lipsarcoma tumors, treated for 2, 2, and 11 cycles, respectively; three patients with ovarian, mesothelioma and colon tumors, treated for 2, 6, and 2 cycles, respectively; three patients with pancreas, ovarian, and breast tumors, treated for 2, 2, and 2 cycles, respectively; three patients with colon, colon, and non-Hodgkin's lymphoma tumors, treated for 8, 2, and 2 cycles, respectively; three patients with ovarian, colon and colon, tumors, treated for 2, 2, and 2 cycles, respectively; three patients with bladder, colon and pancreatic tumors, treated for 2, 2, and 9 cycles, respectively; and four patients with non-small cell lung carcinoma, hepatoma, non-small cell lung carcinoma and renal tumors, treated for 1, 2, 2, and 2 cycles, respectively.

Clinical Responses in Patients with Advanced Cancer-14 Day Continuous Infusion

The toxicity of ISIS 2503 in this study was limited to grade 1–2 fever (10 mg/kg, 2 patients), grade 2 fatigue (10 mg/kg, 2 patients; 4.5 mg/kg, 1 patient) and grade 2 nausea (6 mg/kg, 2 patients). There were no complete or partial responses; 4 patients (liposarcoma, 1.0 mg/kg; mesothelioma, 2.0 mg/kg; colon, 4.5 mg/kg; pancreatic, 8 mg/kg) had stable disease for 10, 6, 8 and 9 cycles, respectively. Preliminary pharmacokinetic analysis demonstrated dose-related increases in steady-state plasma levels of intact ISIS 2503, with levels of 2.22+/−0.99 ug/ml (approximately 320+/−140 nM) at the 4.5 mg/kg dose level. Across the dose range 2.0–4.5 mg/kg, the plasma concentrations revealed that 63–68% of ISIS 2503 remained intact.

The best tumor responses were seen in four patients; one with sarcoma (pelvic masses) wherein stable disease was achieved after 10 cycles at 1.0 mg/kg/d with prior MAID (mesna, doxorubicin, ifosfamide and DTIC) chemotherapy; one with mesothelioma (measurable disease) wherein stable disease was achieved and continued after 4 cycles at 2.0 mg/kg/d with progression after 6 cycles with no prior therapy; one with colon cancer wherein stable disease was achieved after 6 cycles at 4.5 mg/kg/d with progression after 8 cycles, patient having prior surgery and adjuvant 5-Flurouracil+RT; and one patient with pancreatic cancer wherein stable disease was achieved after 8 cycles at 8.0 mg/kg/d but was removed from the study due to hepatic abscess after cycle 9. Progression in the last patient followed prior 5-Fluorouracil+RT with further progression following prior gemcitabine treatment.

Example 21

Reduction of H-ras Expression in Peripheral Blood Mononuclear Cells of Cancer Patients After Treatment with Antisense Oligonucleotide-14 Day Continuous Infusion Patient peripheral-blood mononuclear cells (PBMCS) were analyzed for H-ras mRNA levels after treatment via 14-day continuous intravenous infusion through two cycles. Granulocytes and lymphocytes were separated by density gradient centrifugation of whole blood. Cells were lysed in guanidinium solution, and RNA was isolated by step gradient centrifugation of the cell lysate over 5.7M CsCl. Total cellular RNA was separated on a 1.2% agarose gel and transferred from the gel to a blotting membrane by overnight capillary action. Membranes with bound RNA were hybridized with a random-primed, 32P-labeled RNA probe made using a human H-ras cDNA template. Membranes were washed, and H-ras mRNA was visualized and quantitated by phosphorimage analysis. Results were expressed as a percentage of pre-treatment levels. Reduction of H-ras expression by 20% was seen in 4 out of 6 patients by day 7 in the first cycle and by 30% in 5 out of 6 patients by day 14. In the second cycle reductions of up to 70% were seen in 5 out of 6 patients at day 7 and up to 80% at day 14. Reduced H-ras mRNA expression was observed by Northern blot at both the 1.0 and 2.0 mg/kg dose level.

Example 22

Effects of Antisense Inhibition of H-ras as First-line Therapy in Patients with Advanced Colorectal Carcinoma-14 Day Continuous Infusion A continuous intravenous infusion of ISIS 2503 was administered to 17 evaluable patients with previously untreated stage IV or recurrent colorectal carcinoma (11 male, 6 female; age range 46–81 years) at a dose of 6.0 mg/kg/d by 14-day continuous infusion, repeated every 21 days. These patients received 38 cycles and were evaluated for tumor response after every 3 treatment cycles. Treatment continued until disease progression in patients with objective response or stable disease. Eligibility required an ECOG PS of ≦2 and histologically confirmed cancer with measurable or evaluable solid tumor or lymphoma and no effective therapy. Normal organ function was also required (creatinine≦1.5 mg/dL; bilirubin≦2.0 mg/dL; AST/ALT<2.5× ULN (≦5× in the presence of hepatic metastasis); ANC>1500/mm$^3$; platelet count>100,000/mm$^3$; hemoglobin>9 g/dL and prothrombin time/activated partial thromboplastin (PT/aPTT) normal). Patients also had no underlying disease state associated with active bleeding nor were they on any anti-coagulation therapy or had any uncontrolled CNS involvement by tumor. Pregnant women were also excluded.

ISIS 2503 was supplied as a sterile solution in 1 ml or 10 ml vials containing phosphate buffered saline (pH 7.4) at a concentration of 10 mg/ml. Prior to administration ISIS 2503 was diluted in normal saline for infusion by a volumetric infusion pump with a 0.22 μm in-line filter.

Clinical Responses in Patients with Advanced Colorectal Carcinoma-14 Day Continuous Infusion Toxicity of ISIS 2503 was limited to grade 1–2 fever in the first 24–48 hours after starting the infusion in several patients, and grade 1 thrombocytopenia in 3 patients. The best responses to date are; stable disease, 2 patients (6 and 3 cycles); progressive disease, 5 patients; and too early, 5 patients. Five patients were not evaluable for response. ISIS 2503 was well tolerated at this dose and schedule in patients with advanced colorectal cancer. Accrual is continuing to estimate the activity of single-agent ISIS 2503 in this patient population.

What is claimed is:

1. An oligonucleotide 8 to 30 nucleotides in length which is targeted to a nucleic acid encoding human Ki-ras, wherein said oligonucleotide is capable of inhibiting Ki-ras expression, and wherein said oligonucleotide comprises at least an 8-nucleobase portion of SEQ ID NO: 20, 21, 22, 31, 32 or 33.

2. The oligonucleotide of claim 1 which comprises at least one backbone modification.

3. The oligonucleotide of claim 1 wherein at least one of the nucleotide units of said oligonucleotide is modified at the 2' position of the sugar.

4. The oligonucleotide of claim 1 which is a chimeric oligonucleotide.

5. The oligonucleotide of claim 1 in a pharmaceutically acceptable carrier.

6. A method of modulating the expression of human Ki-ras comprising contacting tissues or cells containing a human Ki-ras gene with an effective amount of an oligonucleotide of 8 to 30 nucleotides in length which is targeted to a nucleic acid encoding human Ki-ras, wherein said oligonucleotide is capable of inhibiting Ki-ras expression, wherein said oligonucleotide comprises at least an 8-nucleobase portion of SEQ ID NO: 20, 21, 22, 26, 28, 31, 32 or 33 and whereby expression of Ki-ras is modulated.

7. A method of inhibiting the proliferation of cancer cells comprising contacting cancer cells with an effective amount of an oligonucleotide 8 to 30 nucleotides in length which is targeted to a nucleic acid encoding human Ki-ras, wherein said oligonucleotide is capable of inhibiting Ki-ras expression, wherein said oligonucleotide comprises at least an 8-nucleobase portion of SEQ ID NO: 20, 21, 22, 26, 28, 31, 32 or 33 and, whereby proliferation of the cancer cells is inhibited.

8. A method of preventing or treating a condition arising from the activation of a Ki-ras oncogene comprising contacting an animal suspected of having a condition arising from the activation of a Ki-ras oncogene with an effective amount of an oligonucleotide 8 to 30 nucleotides in length which is targeted to a nucleic acid encoding human Ki-ras, wherein said oligonucleotide is capable of inhibiting Ki-ras expression, wherein said oligonucleotide comprises at least an 8-nucleobase portion of SEQ ID NO: 20, 21, 22, 26, 28, 31, 32 or 33 and, whereby said condition is prevented or treated.

9. The method of claim 8 wherein said activation of a Ki-ras oncogene is abnormal expression of a Ki-ras oncogene.

10. The method of claim 8 wherein said condition is a hyperproliferative condition.

11. The method of claim 8 wherein the condition is cancer.

12. The method of claim 8 wherein the condition is colorectal cancer, melanoma, liposarcoma, mesothelioma, sarcoma, colon cancer, or pancreatic cancer.

13. The method of claim 6 wherein the cells are cancer cells.

14. The method of claim 6 wherein the cells are blood cells.

15. The method of claim 6 wherein the cells are peripheral blood mononuclear cells.

* * * * *